United States Patent
Rotin et al.

(10) Patent No.: US 9,120,768 B2
(45) Date of Patent: Sep. 1, 2015

(54) COMPOSITIONS AND METHODS FOR TREATMENT OF CYSTIC FIBROSIS AND DISEASES ASSOCIATED WITH ABERRANT PROTEIN CELLULAR PROCESSING

(75) Inventors: Daniela Rotin, Toronto (CA); Agata Trzcinska-Daneluti, Toronto (CA)

(73) Assignee: The Hospital for Sick Children, Toronto, Ontario (CA)

( * ) Notice: Subject to any disclaimer, the term of this patent is extended or adjusted under 35 U.S.C. 154(b) by 89 days.

(21) Appl. No.: 13/817,848

(22) PCT Filed: Aug. 19, 2011

(86) PCT No.: PCT/CA2011/000934
§ 371 (c)(1),
(2), (4) Date: Feb. 20, 2013

(87) PCT Pub. No.: WO2012/021974
PCT Pub. Date: Feb. 23, 2012

(65) Prior Publication Data
US 2013/0150422 A1    Jun. 13, 2013

Related U.S. Application Data

(60) Provisional application No. 61/375,668, filed on Aug. 20, 2010.

(51) Int. Cl.
*C07D 403/06* (2006.01)
*C07D 313/00* (2006.01)
*A61K 31/015* (2006.01)
*A61K 31/404* (2006.01)

(52) U.S. Cl.
CPC ............ *C07D 403/06* (2013.01); *A61K 31/015* (2013.01); *A61K 31/404* (2013.01); *C07D 313/00* (2013.01)

(58) Field of Classification Search
CPC .................................................. C07D 403/06
See application file for complete search history.

(56) References Cited

U.S. PATENT DOCUMENTS

| | | |
|---|---|---|
| 3,373,030 A | 3/1968 | Hodge et al. |
| 3,551,454 A | 12/1970 | Tauh et al. |
| 3,810,918 A | 5/1974 | Urry et al. |
| 3,836,544 A | 9/1974 | Urry et al. |
| 3,925,423 A | 12/1975 | Hodge |
| 5,795,910 A | 8/1998 | Giese et al. |
| 6,906,093 B2 | 6/2005 | Tang et al. |
| 2010/0204211 A1 | 8/2010 | Park et al. |

FOREIGN PATENT DOCUMENTS

| | | |
|---|---|---|
| WO | WO2007/014327 | 2/2007 |
| WO | WO2008/021213 | 2/2008 |

OTHER PUBLICATIONS

Burgel PR, Nadel JA. Epidermal growth factor receptor-mediated innate immune responses and their roles in airway diseases. Eur Respir J. Oct. 2008;32(4):1068-81.*
Nagaraj NS, Singh OV, Merchant NB. Proteomics: a strategy to understand the novel targets in protein misfolding and cancer therapy. Expert Rev Proteomics. Aug. 2010;7(4):613-23. Review. PubMed PMID: 20653514.
Kalin, N. et al. DeltaF508 CFTR Protein Expression in Tissues from Patients with Cystic Fibrosis. The Journal of Clinical Investigation. 103(10):1379-1389, 1999.
Wendeler, MW. et al. Improved Maturation of CFTR by an ER Export Signal. FASEB J. 21:2352-2358, 2007.
Thulasiraman V. et al. In Vivo newly translated polypeptides are Sequestered in a Protected Folding Environment. The EMBO Journal. 18(1):85-95, 1998.

\* cited by examiner

*Primary Examiner* — Paul Zarek
(74) *Attorney, Agent, or Firm* — Bereskin & Parr LLP/S.E.N.C.R.L., s.r.l.

(57) ABSTRACT

The disclosure relates to resorcylic acid lactones and indolinone-containing compounds for use in treatment of diseases associated with aberrant protein processing, such as cystic fibrosis (CF; mucoviscidosis). The disclosure more generally relates to treatment of aberrant protein processing, such as errors in protein folding, trafficking or post-translational modification.

7 Claims, 7 Drawing Sheets

Effect of (5Z)-7-oxozeaenol, SU5402 and SU6668 on the cell surface expression of delF508-CFTR

Effect of (5Z)-7-oxozeaenol, SU5402 and SU6668 on delF508-CFTR chloride channel activity in MDCK cells Effect of SU6668 on delF508-CFTR chloride channel activity in primary human bronchial epithelial (HBE) cells

US 9,120,768 B2

COMPOSITIONS AND METHODS FOR TREATMENT OF CYSTIC FIBROSIS AND DISEASES ASSOCIATED WITH ABERRANT PROTEIN CELLULAR PROCESSING

The disclosure relates to resorcylic acid lactones and indolinone-containing compounds for use in treatment of diseases associated with aberrant protein processing, such as cystic fibrosis (CF; mucoviscidosis). The disclosure more generally relates to treatment of aberrant protein processing, such as errors in protein folding, trafficking or post-translational modification. The disclosure also relates to restoration of trafficking of proteins from the endoplasmic reticulum (ER) to the plasma membrane of the cells.

BACKGROUND

Cystic fibrosis (CF; mucoviscidosis) is the most common genetic disorder in the Caucasian population, affecting 1:2500 live births[1]. CF is associated with a wide-spread defect in the secretory processes of all secretory epithelia, including abnormalities in airways, gastrointestinal and genitourinary tracts and elevated sweat electrolyte concentrations. The blockage of the airways and pancreatic ducts due to abnormally viscous mucous secretions are responsible for the two most clinically important manifestations of CF, that being chronic pulmonary infection and pancreatic insufficiency.

The above manifestations appear related to abnormal ion transport in the secretory epithelia of the affected organs such as sinuses, lungs, pancreas, liver, and reproductive tract[1-10]. The relative impermeability of epithelial cell membranes to $Cl^-$ ions appears to be the primary defect in CF.

CF is caused by mutations in the cystic fibrosis gene (CFTR) located on the long arm of chromosome 7 at position q31. CFTR encodes a 1480 amino acid polypeptide, called Cystic Fibrosis Transmembrane Conductance Regulator (CFTR), which functions as a chloride channel in epithelial membranes[11-14]. Besides its function as a chloride channel, CFTR regulates other apical membrane conductance pathways[15].

The CFTR protein in healthy individuals is found in the apical membrane of epithelial cells, which lines the airways, gastrointestinal tract, and other exocrine ducts in the body. The CFTR protein is composed of 12 transmembrane domains (TMDs), two cytosolic nucleotide-binding domains (NBDs), and a cytosolic R region that contains multiple sites for cAMP-dependent phosphorylation[16,17]. Transport of anions through the transmembrane helices is controlled by the NBDs. It is believed that these domains interact with two molecules of ATP to form a dimer and that binding/hydrolysis of ATP molecules control CFTR channel opening[18]. The CFTR chloride channel is phosphorylated by protein kinase A (PKA). Phosphorylation by PKA has only a minor effect on CFTR ATPase activity[19] and apparently does not act primarily by influencing binding or hydrolysis of the ATP ligand[20] but does promote the association of the two NBDs[21].

While several classes of mutation in CFTR have been identified to date, the most common mutation found in >90% of patients of European ancestry is a deletion of Phenylalanine at position 508 (delF508-CFTR)[1,22]. The F508 deletion, located in NBD1, alters the folding and prevents the full maturation of the delF508-CFTR protein, which is therefore degraded very early during biosynthesis. This abnormal folding of the delF08-CFTR mutant protein is thought to be responsible for its improper cellular localization. As delF508-CFTR is a trafficking-impaired mutant that is retained in the ER, its levels at the apical membrane are reduced dramatically, precluding proper $Cl^-$ secretion, which leads to CF[23-25].

Over the past few years, several small molecules have been identified that attempt to correct the trafficking and functional defects of the delF508-CFTR mutant, such as compounds 3a and 4a (corr-4-a)[26-30], carboplatin, sildenafil or its analogues[31-32], VRT-325 and VRT-640[33-34]. Some of these compounds (e.g. VRT(VX)-809 or VX-770) are now in pre-clinical trials.

Current therapies for the treatment of CF are directed toward treatment of the symptoms or effects of the disease and target the secondary effects of the disease; namely, obstructed airways, malnutrition, and chronic bacterial infections in the lungs. These approaches do not address the primary defect of the disease, the mutant CFTR protein, and thereby the reduced chloride channel activity.

SUMMARY OF THE INVENTION

The present disclosure provides compounds useful for treating diseases associated with cellular processing of proteins (e.g. folding, trafficking, or post-translational modification) errors, primarily cystic fibrosis.

The inventors have found that the resorcylic acid lactones and indolinone derivatives restore trans-membrane transport capacity of the major mutated forms of CFTR (e.g. delF508-CFTR) by correcting cellular processing of the mutant (i.e. inducing the translocation to the plasma membrane). Resorcylic acid lactones and indolinone derivatives re-direct the mutant CFTR protein to the plasma membrane of the cells, where its $Cl^-$ transport activity is stimulated by physiological agonists.

The disclosure is further directed to pharmaceutical compositions comprising a therapeutically effective amount of the aforementioned compounds together with a pharmaceutically acceptable carrier or excipient. As opposed to the current CF therapies, the compositions of the present invention address the primary defect of the CF disease (i.e. the mutant CFTR protein and the reduced chloride channel activity), thus are useful for the treatment of cystic fibrosis.

In certain embodiments, the disclosure also relates to uses and methods of treatment of a subject with reduced function protein, such as reduced function CFTR, by administering a compound described herein to the subject. Optionally the subject is a mammal, more typically a human. Optionally the reduced function protein is misfolded protein (e.g. mutant protein) such as misfolded mutant CFTR (e.g. delF508-CFTR).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF DRAWINGS

Embodiments of the disclosure will be described in relation to the drawings in which.

Average normalized fluorescent values of delF508-CFTR expressed in 293MSR-GT cells (which co-express eYFP (H148Q/I152L) that are treated with 10 μM (5Z)-7-oxozeaenol (a) or SU5402 (b), as indicated, and grown at 37° C. After 48 hrs cells are stimulated with FIG (25 μM Forskolin, 500 μM IBMX and 50 μM Genistein) and fluorescent quenching during Cl⁻/I⁻ exchange of 100-300 cells is quantified simultaneously and recorded. Data are average of triplicate wells, with 100-300 cells analyzed per well. (c) Increase in delF508-CFTR chloride channel activity identified as the difference in Average Fluorescence Intensity ($\Delta FI_{avg}$) after stimulation with FIG.

Figure 2:
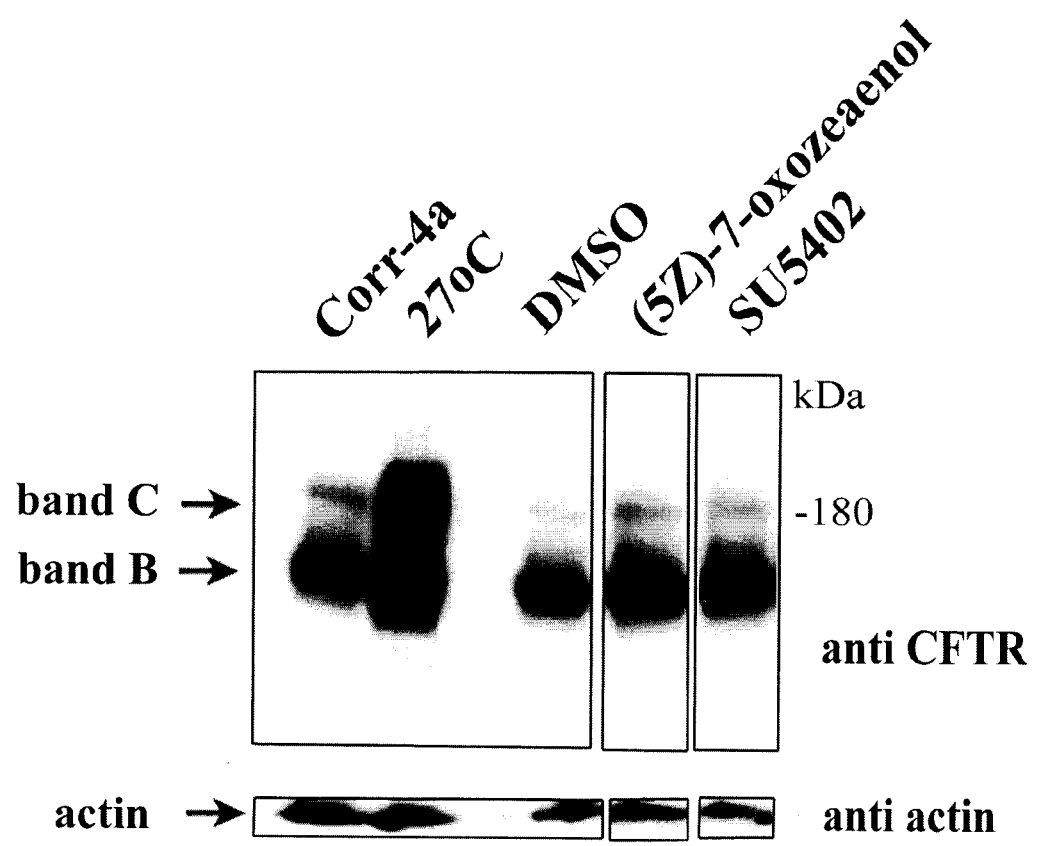

FIG. 2: Effect of (5Z)-7-Oxozeaenol and SU5402 on delF508-CFTR Maturation Analyzed by Immunoblotting.

293MSR-GT cells stably expressing delF508-CFTR were treated with 10 μM (5Z)-7-oxozeaenol, SU5402, corr-4-a (positive control) or 0.2% DMSO (negative control), as indicated, grown at 37° C. for 48 hrs, and the appearance of the mature protein, band C, monitored by immunoblotting with anti-CFTR antibodies. Band B represents the immature protein. DMSO represents negative control (vehicle-alone) and 27° C. represents temperature rescue of delF508-CFTR at 27° C. Top panel depicts the anti-CFTR immunoblot, bottom panel depicts actin (loading) control.

Figure 3:
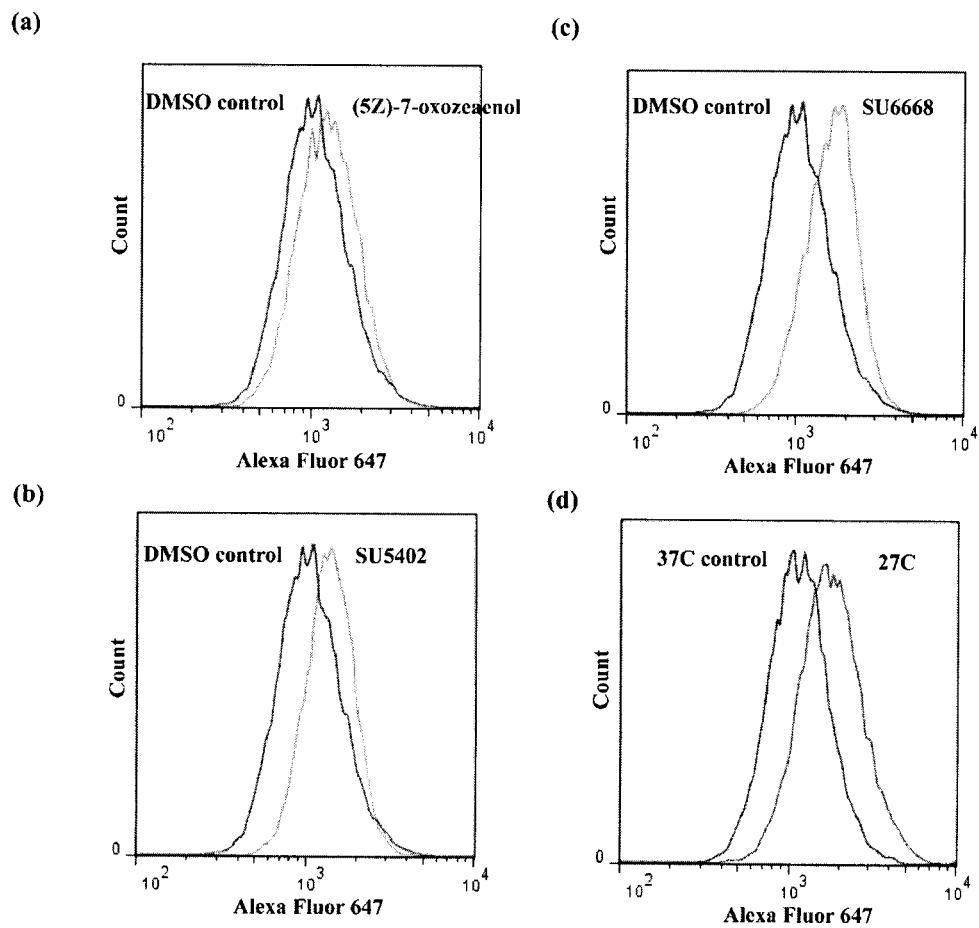

FIG. 3: Effect of (5Z)-7-Oxozeaenol, SU5402 and SU6668 on Cell Surface Expression of delF508-CFTR Analyzed by Flow Cytometry.

BHK cells stably expressing delF508-CFTR-3HA were treated with 0.2% DMSO (negative control), 10 μM (5Z)-7-oxozeaenol (a), SU5402 (b) SU6668 (c) or placed at 27° C. (positive control) (d) for 48 hrs. Flow cytometry was then performed on non-permeabilized cells following immunostaining for the HA epitope located at the ectodomain of delF508-CFTR, to quantify the amount of cell-surface delF508-CFTR in the treated cells.

Figure 4:
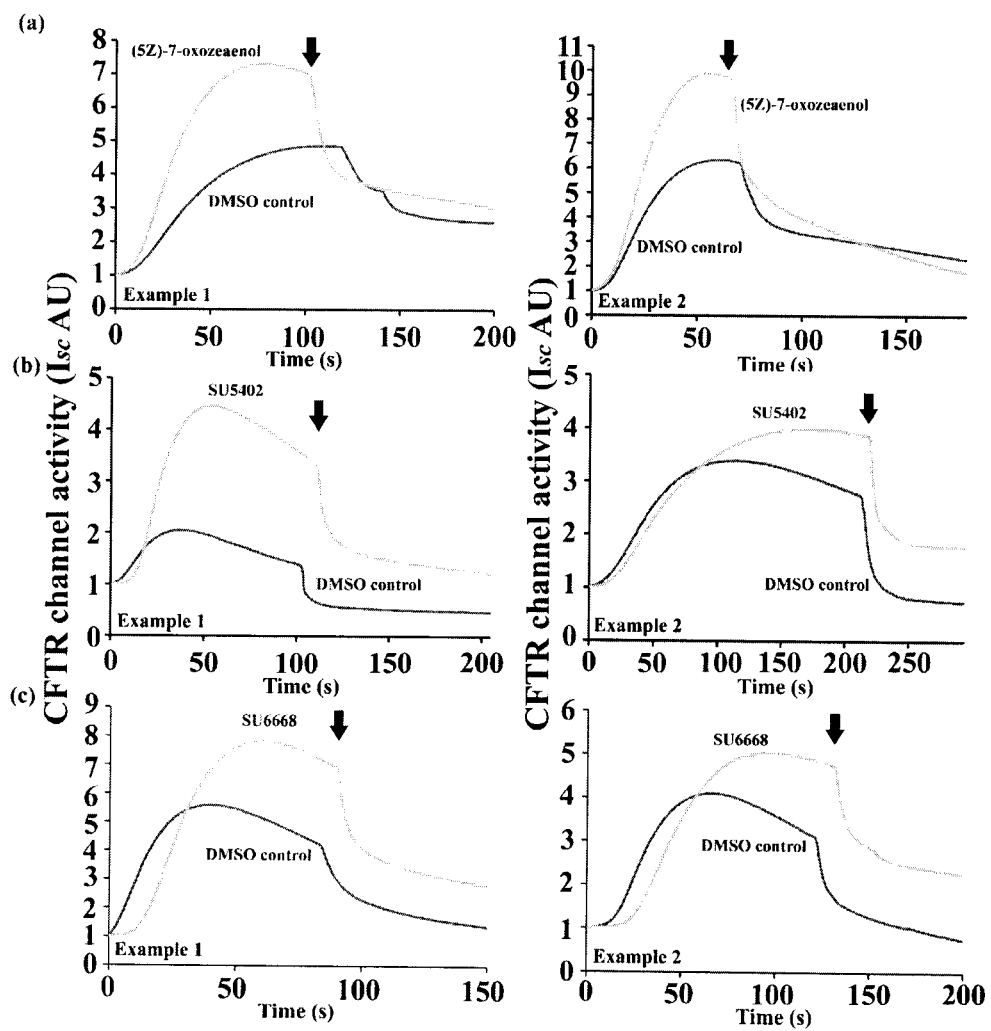

FIG. 4: Effect of (5Z)-7-Oxozeaenol, SU5402 and SU6668 on delF508-CFTR Chloride Channel Activity in Epithelial MDCK Cells Stably Expressing delF508-CFTR.

Representative normalized short-circuit current traces on MDCK delF508-CFTR monolayers treated with 10 μM (5Z)-7-oxozeaenol (a), SU5402 (b) or SU6668 (c) for 48 hrs prior to analysis in Ussing chambers. ENaC sodium channels were inhibited with 10 μM amiloride; non-CFTR chloride channels were blocked with 300 μM DNDS. CFTR currents were stimulated with FIG (25 μM Forskolin, 25 μM IBMX and 50 μM Genistein) at time 0 and after the indicated times (arrows) inhibited using 15 M GlyH-101. AU, arbitrary units.

Figure 5:
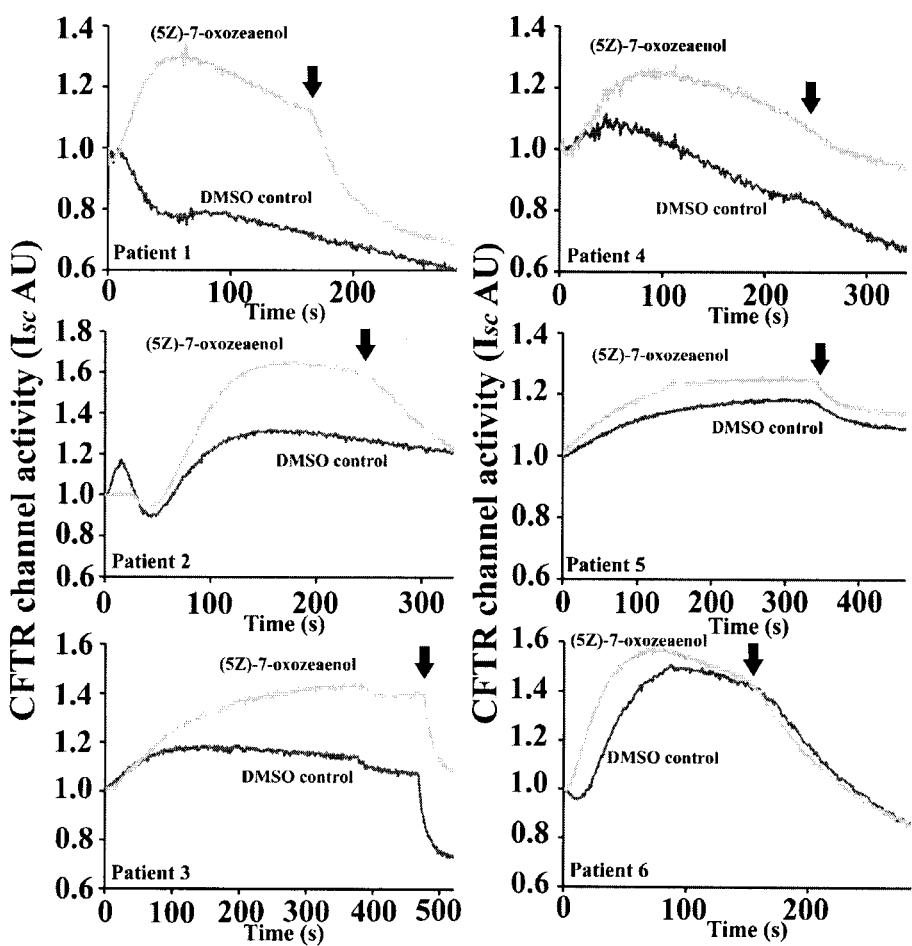

FIG. 5: Effect of (5Z)-7-Oxozeaenol on delF508-CFTR Chloride Channel Activity in Primary Human Bronchial Epithelial (HBE) Cells Harvested from Lungs of delF508/delF508 Homozygote Patients Undergoing Lung Transplant.

Representative normalized short-circuit currents mediated by delF508-CFTR bronchial epithelial monolayers obtained from patients homozygous for the deletion of F508. The delF508-CFTR monolayers were treated with 10 μM (5Z)-7-oxozeaenol for 48 hrs prior to analysis in Ussing chambers. ENaC sodium channels were inhibited with 10 μM amiloride; non-CFTR chloride channels were blocked with 300 μM DNDS. CFTR currents were stimulated with FIG (25 M Forskolin, 25 M IBMX and 50 μM Genistein) at time 0 and after the indicated times (arrows) inhibited using 50 μM CFTRinh-172. AU, arbitrary units.

Figure 6:
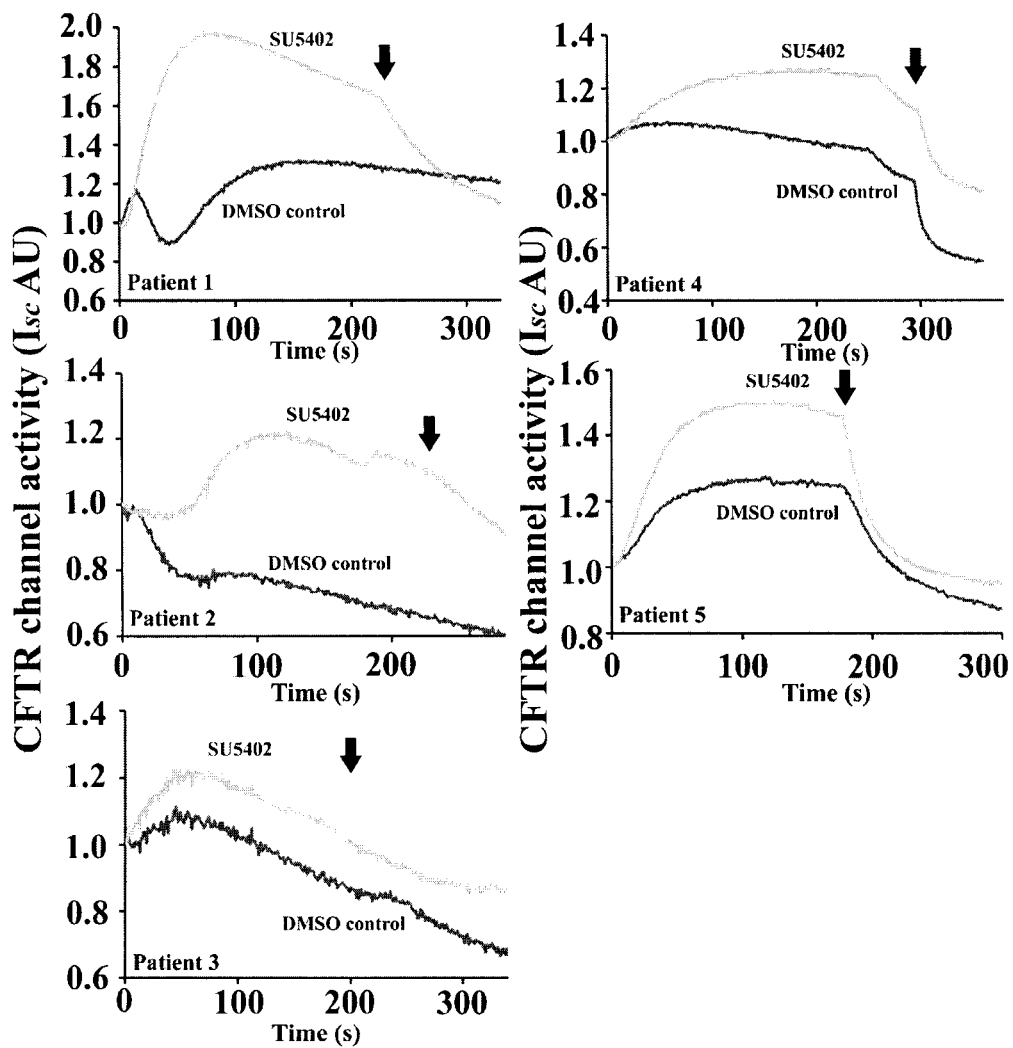

FIG. 6: Effect of SU5402 on delF508-CFTR Chloride Channel Activity in Primary Human Bronchial Epithelial (HBE) Cells Harvested from Lungs of delF508/delF508 Homozygote Patients Undergoing Lung Transplant.

Representative normalized short-circuit currents mediated by delF508-CFTR bronchial epithelial monolayers obtained from patients homozygous for the deletion of F508. The delF508-CFTR monolayers were treated with 10 μM SU5402 for 48 hrs prior to analysis in Ussing chambers. ENaC sodium channels were inhibited with 10 μM amiloride; non-CFTR chloride channels were blocked with 300 μM DNDS. CFTR currents were stimulated with FIG (25 M Forskolin, 25 M IBMX and 50 μM Genistein) at time 0 and after the indicated times (arrows) inhibited using 50 μM CFTRinh-172. AU, arbitrary units.

Figure 7:
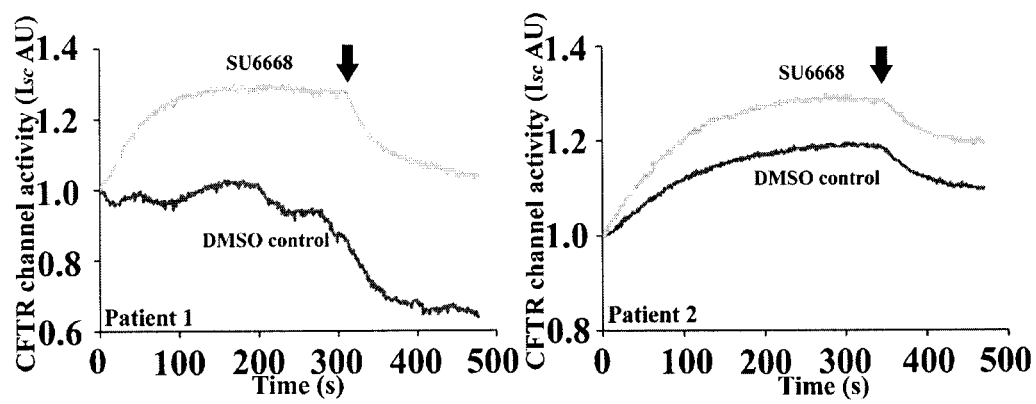

FIG. 7: Effect of SU6668 on delF508-CFTR Chloride Channel Activity in Primary Human Bronchial Epithelial (HBE) Cells Harvested from Lungs of delF508/delF508 Homozygote Patients Undergoing Lung Transplant.

Representative normalized short-circuit currents mediated by delF508-CFTR bronchial epithelial monolayers obtained from patients homozygous for the deletion of F508. The delF508-CFTR monolayers were treated with 10 μM SU6668 for 48 hrs prior to analysis in Ussing chambers. ENaC sodium channels were inhibited with 10 μM amiloride; non-CFTR chloride channels were blocked with 300 μM DNDS. CFTR currents were stimulated with FIG (25 μM Forskolin, 25 μM IBMX and 50 μM Genistein) at time 0 and after the indicated times (arrows) inhibited using 50 μM CFTRinh-172. AU, arbitrary units.

DETAILED DESCRIPTION

Definitions

"CF" refers to cystic fibrosis (mucoviscidosis). "CFTR" refers to the Cystic Fibrosis Transmembrane Conductance Regulator. In one embodiment the CFTR is mammalian CFTR or, more specifically, human CFTR, a 1,480 amino acid protein.

"CFTR" refers to the Cystic Fibrosis Transmembrane Conductance Regulator, whether wild type or mutant.

"Wild type" refers to a native or non-mutant sequence, typically a protein sequence. Wild type CFTR refers to native CFTR, and particularly native mammalian CFTR (mCFTR) or human CFTR (hCFTR) that has normal chloride channel activity in a membrane. "Wild type sequence" refers to a native primary amino acid sequence. For example, the wild type polypeptide sequence of human CFTR is provided under accession number P13569. "Wild type conformation" refers to the normal, native secondary and tertiary structure of a specific protein. For example, the CFTR structure for the wild type NBD1 and NBD2 domains are at the following PDB IDs: 1NBD; 2PZG; 2PZE; 3GD7. Wild type folded CFTR is optionally referred to as "natively folded" CFTR, "normally folded" CFTR and/or "properly folded" CFTR.

"Misfolded" refers to the secondary and tertiary structure of a protein, and indicates that the protein has adopted a conformation that is not normal for that protein in its properly functioning state. Although misfolding can be caused by mutations in a protein, such as amino acid deletion, substitution, or addition, wild-type sequence protein can also be misfolded in disease, for instance, as a result of microenvironmental conditions and/or amino acid modification such as nitration, oxidation, carbonylation or other modification. One example of a misfolded, mutant human CFTR has a deletion of Phenylalanine at position 508 (delF508-CFTR) (a class 2 deletion).[1,22]

"Mutant" refers to non-wild type sequence, typically a protein sequence, that occurs as a result of genetic mutation that results in amino acid substitution or deletion, such as those substitutions/deletions characteristic of CF. Examples of mutant CFTR genes and proteins that lead to non-functional CFTR are also listed in accession no. P13569.

"Fully functional protein" refers to normally functioning, native protein. Fully functional CFTR protein must be in a membrane to demonstrate its fully functional CFTR activity by transporting chloride ions at normal levels. It is understood by one of skill in the art that not all fully functional, wild type CFTR expressed in healthy humans is necessarily transported to a membrane.

"Reduced function protein" refers to a non-wild type protein that has reduced functionality compared to wild type, or no functionality. Reduced function is typically due to mutation or due to aberrant cellular processing of proteins (e.g. errors in folding, trafficking, or post-translational modification). Reduced function CFTR has reduced functionality compared to wild type CFTR, or no functionality, as a chloride channel for transporting chloride ions. For example, reduced function CFTR may be transported to the cell membrane at a lower rate compared to wild type, or not at all. If reduced function CFTR is in a cell membrane, it may have reduced stability or it may have reduced, or no, chloride channel activity. One example of a non-functional, mutant human CFTR affected by aberrant processing is delF508-CFTR which is a trafficking impaired mutant of CFTR protein that is retained in the ER and targeted for degradation.

The term "pharmaceutically acceptable" means compatible with the treatment of animals or, in particular, humans.

"Pharmaceutically acceptable derivatives" of a compound of the invention include, but are not limited to, salts, esters, enol ethers, enol esters, acids, bases, solvates, hydrates or prodrugs thereof. Such derivatives may be administered to humans or animals without substantial toxic effects and either are pharmaceutically active or are prodrugs.

"Pharmaceutically acceptable salt" refers to those salts which retain the biological effectiveness and properties of the free bases and which are obtained by reaction with inorganic and organic acids such as hydrochloric acid, hydrobromic acid, sulfuric acid, phosphoric acid, methanesulphonic acid, trifluoromethanesulfonic acid, benzenesulfonic acid, 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include salts of inorganic bases, such as salts containing alkaline cations (e.g., $Li^+Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

"Pharmaceutically acceptable ester" refers to an ester that is pharmaceutically acceptable and that possesses the desired pharmacological activity of the parent compound, and includes, but is not limited to, alkyl, alkenyl, allynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

"Pharmaceutically acceptable enol ether" refers to an enol ether that is pharmaceutically acceptable and that possesses the desired pharmacological activity of the parent compound, and includes, but is not limited to, derivatives of formula $C=C(OR)$ where R is hydrogen, alkyl, alkenyl, alkynyl, aryl, heteroaryl, aralkyl, heteroaralkyl, cycloalkyl or heterocyclyl.

"Pharmaceutically acceptable enol ester" refers to an enol ester that is pharmaceutically acceptable and that possesses the desired pharmacological activity of the parent compound, and includes, but is not limited to, derivatives of formula $C=C(OC(O)R)$ where R is hydrogen, alkyl, alkenyl, alkynyl, aryl, heteroaryl, aralkyl, heteroaralkyl, cycloalkyl or heterocyclyl.

"Pharmaceutically acceptable solvate or hydrate" refers to a solvate or hydrate complex that is pharmaceutically acceptable and that possesses the desired pharmacological activity of the parent compound, and includes, but is not limited to, complexes of a compound of the invention with one or more solvent or water molecules.

"Prodrugs" refer to the compounds of the invention that are further modified with labile functional groups. Those groups are cleaved after in vivo administration to furnish the parent active agent. Prodrugs, can be used, for example, to alter the physicochemical properties of the active agent, to target the active agent to a specific tissue, to reduce undesirable side effects and/or to alter the pharmacokinetic and pharmacodynamic properties of the active agent (e.g. solubility, absorption, biostability and release time)[35].

The term "stereoisomer" as used herein means an isomer that possesses identical constitution as a corresponding stereoisomer, but which differs in the arrangement of its atoms in space from the corresponding stereoisomer. For example, stereoisomers may be enantiomers, diastereomers and/or cis-trans (E/Z) isomers. It should be understood that a composition comprising compounds of the disclosure may comprise single enantiomers, single diastereomers as well as mixtures thereof at any ratio (for example racemic mixtures, non-racemic mixtures, mixtures of at least two diastereomers and so forth).

"Alkyl" refers to a straight-chain or branched saturated aliphatic hydrocarbon. In an embodiment, the alkyl group has 1 to 20 carbons. In a further embodiment, it is a lower alkyl of from 1 to 10 carbons, or 1 to 7 carbons, or 1 to 4 carbon atoms. Typical alkyl groups include methyl, ethyl, propyl, isopropyl, butyl, isobutyl, tertiary butyl, pentyl, hexyl and the like. The alkyl group may be optionally substituted with one or more substituents selected from the group consisting of hydroxyl, cyano, alkoxy, $=O$, $=S$, $NO_2$, halogen, $N(CH_3)_2$, $NH_2$, and SH.

"Alkanoyl" refers to an acyl group C(O)alkyl.

"Alkoxy" refers to an "-Oalkyl" or "Ocycloalkyl" group.

"Aryl" refers to an aromatic group, which has at least one ring having a conjugated pi electron system and includes carbocyclic aryl, and biaryl groups, and contains between 6 and 14 carbon atoms, or 6 to 10 carbon atoms, or 6 carbon atoms The aryl group may be optionally substituted with one or more substituents selected from the group consisting of halogen, trihalomethyl, hydroxyl, SH, OH, $NO_2$, amine, thioether, cyano, alkoxy, alkyl, and $NH_2$. Typical aryl groups include phenyl, naphthyl, etc.

"Alkaryl" or "alkheteroaryl" refers to an alkyl that is covalently joined to an aryl or heteroaryl group. In an embodiment, the alkyl is a lower alkyl.

"Carbocyclic aryl" refers to an aryl group wherein the ring atoms are carbon.

"Cycloalkyl" refers to a cyclic saturated aliphatic hydrocarbon. In an embodiment, the cycloalkyl group has 3 to 10 carbons. In a further embodiment, it is a lower alkyl of from 3 to 7 carbons, or 4 to 6 carbons. Typical cycloalkyl groups include cyclopropyl, cyclobutyl, cyclopentyl, cyclohexylhexyl and the like. The cycloalkyl group may be optionally substituted with one or more substituents selected from the group consisting of hydroxyl, cyano, alkoxy, =O, =S, $NO_2$, halogen, $N(CH_3)_2$, $NH_2$, and SH "Halogen" refers to the fluoro, chloro, bromo or iodo groups. There can be one or more halogen groups, which are the same or different.

"Heterocyclic aryl" or "heteroaryl" refers to an aryl group having from 1 to 3 heteroatoms as ring atoms, the remainder of the ring atoms being carbon, and having between 5 and 14 atoms in total, or between 5 and 10 atoms, or between 5 and 6 atoms in total. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Amide" refers to —C(O)—NH—R, where R is alkyl, cycloalkyl, aryl, heteroaryl, alkylaryl, alkheteroaryl or hydrogen.

"Amine" refers to a —N($R^a$)$R^b$ group, where $R^a$ and $R^b$ are independently selected from the group consisting of alkyl, cycloalkyl, aryl, heteroaryl, alkylaryl or alkheteroaryl.

"Thioether" refers to —S—R, where R is alkyl, cycloalkyl, aryl, heteroaryl, alkylaryl or alkheteroaryl.

The term a "therapeutically effective amount", "effective amount" or a "sufficient amount" of a compound is a quantity sufficient to, when administered to the subject, including a mammal, for example a human, effect beneficial or desired results, including clinical results, and, as such, an "effective amount" or synonym thereto depends upon the context in which it is being applied. In the context of disease, therapeutically effective amounts of a compound is used to treat, modulate, attenuate, reverse, or affect a disease or conditions for example, CF in a subject. An "effective amount" is intended to mean that amount of a compound that is sufficient to treat, prevent or inhibit such diseases or conditions. The amount of a given compound that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" or "effective amount" of a compound is an amount which prevents, inhibits, suppresses or reduces a disease or conditions for example, CF as determined by clinical symptoms, in a subject as compared to a control.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Moreover, a "treatment" or "prevention" regime of a subject with a therapeutically effective amount of the compound may consist of a single administration, or alternatively comprise a series of administrations. For example, a compound may be administered at least once a week. However, in another embodiment, the compound may be administered to the subject from about one time per week to about once daily for a given treatment. In yet another embodiment the compound may be administered more than once daily up to 5 times per day. The length of the treatment period depends on a variety of factors, such as the severity of the disease, the age of the patient, the concentration and the activity of the compounds, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

The present disclosure provides compounds useful for treating diseases associated with cellular processing of proteins (e.g. folding, trafficking, or post-translational modification) errors, primarily cystic fibrosis. The list of diseases identified as being conformational disorders, caused by mutations that alter protein folding and retardation of the mutant protein in the ER, resulting in protein deficiency includes, but is not limited to: Cystic fibrosis, α1-antitrypsin deficiency (hereditary emphysema), Congenital hyperinsulinism, Nephrogenic diabetes insipidus, Neurohypophyseal diabetes insipidus, Retinitis pigmentosa, Hereditary hemochromatosis, Type I hereditary angioedema, Congenital long QT syndrome, Persistent hyperinsulinemic hypoglycemia of infancy (PHHI), Familial hypercholesterolemia, Congenital sucrase-isomaltase deficiency, Crigler-Najjar type II, Diabetes mellitus, Laron syndrome, Hereditary myeloperoxidase, Primary hypothyroidism, Tyroxine binding globulin deficiency, Familial hypercholesterolemia, Familial chylomicronemia, Abeta-lipoproteinema, certain cancers which grow and metastasize as a result of misfolded proteins, especially the p53 protein (see Nagaraj N S, Singh O V, Merchant N B. Proteomics: a strategy to understand the novel targets in protein misfolding and cancer therapy. Expert Rev Proteomics. 2010 August; 7(4):613-23. Review. PubMed PMID: 20653514), Low plasma lipoprotein a, Congenital hypothyroidism, Hereditary hypofibrinogenemia, Alpha-1-antichymotrypsin (ACT) deficiency, von Willebrand disease type IIA, Brugada syndrome, Congenital nephritic syndrome of the finnish type, Dubin-Johnson syndrome, Dravet syndrome (epilepsy; see Patino G A, Claes L R, Lopez-Santiago L F, Slat E A, Dondeti R S, Chen C, O'Malley H A, Gray C B, Miyazaki H, Nukina N, Oyama F, De Jonghe P, Isom L L. A functional null mutation of SCN1B in a patient with Dravet syndrome. J. Neurosci. 2009 Aug. 26; 29(34):10764-78. PubMed PMID: 19710327; PubMed Central PMCID: PMC2749953), X-linked hypophosphatemia (XLH), Pendred syndrome, Hereditary spherocytosis, Pseudoachondroplasia (PSACH) and Multiple epiphyseal (EDM1), Stargardt-like macular dystrophy, Aspartyl-glucosaminuria (AGU), neurodegenerative pathological conditions such as Parkinson's disease, Alzheimer's disease, Charcot-Marie-Tooth syndrome, Pelizaeus-Merzbacher disease, Aceruloplasminemia, Infantile neuronal ceroid lipofuscinosis (ICNL), Fabry disease, Tay-Sachs, Osteogenesis, Carbohydrate-deficient glycoprotein syndrome, Maroteaux-Lamy syndrome, Hereditary blindness, Glanzmann thrombasthenia, Hereditary factor VII deficiency, Oculocutaneous albinism, Adrenoleukodystrophy (ALD) and Protein C deficiency[36,37]. The disclosure also relates to methods and uses of the compounds described herein to increase CFTR chloride channel activity in a cell, tissue or a subject by administration of a compound to a cell tissue or a subject. The disclosure also relates to methods and uses of the compounds described herein to increase the cell surface expression of CFTR, such as delF508-CFTR, in human respiratory epithelial cells by administration of a compound to a cell tissue or a subject. In one embodiment, the compounds correct the trafficking defect of a class 2 mutation of the CFTR protein. In one embodiment, the compound corrects the trafficking defect of the delF508-CFTR mutant protein.

The compounds disclosed in this application are related to zeaenol of the resorcylic acid lactones family ("RALs") and indolinone-containing compounds, known in particular for their anti-inflammatory and anti-proliferative effects[38-40]. RALs are mycotoxins produced by a variety of different fungal strains via polyketide biosynthesis[41]. Some of RALs are available as biological products of fermentation, and others can be obtained by chemical modification of the initial biologic products. The biologic and chemical synthetic techniques for RALs are described in a number of U.S. patents, including U.S. Pat. Nos. 3,373,030, 3,551,454, 3,810,918, 3,836,544, and 3,925,423, 5,795,910, all of which are herein incorporated by reference.

RALs are endowed with diverse biological activity ranging from transcription factor modulators (zearalenone and zearalenol) to HSP90 inhibitors (radicicol and pochonin D) and reversible (aigialomycin D) as well as irreversible kinase inhibitors (RALs containing a cis-enone). Several RALs containing a cis-enone (hypothemycin, LL-Z1640-2 and LL-783277) have been reported to inhibit irreversibly mitogen activated protein kinases (MAP kinases) and be competitive with ATP.

In an illustrative embodiment, the resorcylic acid lactone-containing compound has the formula (I) below including all stereoisomers, polymorphs, metabolites and pharmaceutically acceptable derivatives such as, but not limited to, pharmaceutically acceptable salts, esters, hydrates, prodrugs, solvates (see Definitions section) or combinations thereof:

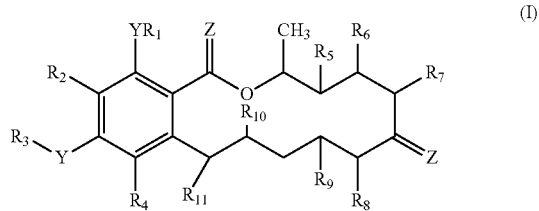

(I)

wherein $R_1$, $R_3$ are each independently H, alkyl, cycloalkyl, aryl, heteroaryl or alkanoyl;

$R_2$, $R_4$ are each independently selected from the group consisting of H, alkyl, cycloalkyl, alkoxy, cycloalkoxy, aryl, heteroaryl, aryloxy, heteroaryloxy, alkaryl, alkheteroaryl, alkaryloxy, alkheteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' and n is 0-3; R is H, alkyl, cycloalkyl, aryl or heteroaryl; R' is H, alkyl, cycloalkyl, aryl or heteroaryl;

Y is O or NR" and each R" independently represents H, alkyl, cycloalkyl, aryl, heteroaryl or alkanoyl;

$R_5$ is H, alkyl or cycloalkyl;

$R_6$, $R_7$ together represent a cis double bond or —O— or each of $R_6$ and $R_7$ independently represents H or OR'" and each R'" independently represents H, alkyl, cycloalkyl, aryl, heteroaryl or alkanoyl;

$R_8$, $R_9$ together represent a double bond or —O— or each of $R_8$ and $R_9$ independently represents H or OR'" and each R'" independently represents H, alkyl, cycloalkyl, aryl, heteroaryl or alkanoyl;

$R_{10}$, $R_{11}$ together represent a double bond or —O— or each of $R_{10}$ and $R_{11}$ independently represents H or OR'" and each R'" independently represents H, alkyl, cycloalkyl, aryl, heteroaryl or alkanoyl; and Z is O, S, —OR'" or —SR'"; and each R'" independently represents H, alkyl, cycloalkyl, aryl, heteroaryl or alkanoyl.

In another embodiment, the compound of the formula (I) has the following definitions:

$R_1$, $R_3$ are each independently H, $(C_{1-20})$-alkyl, $(C_{3-10})$-cycloalkyl, $(C_{6-14})$-aryl, $(C_{5-14})$-heteroaryl or $(C_{1-20})$-alkanoyl;

$R_2$, $R_4$ are each independently selected from the group consisting of H, $(C_{1-20})$-alkyl, $(C_{3-10})$-cycloalkyl, $(C_{1-20})$-alkoxy, $(C_{3-10})$-cycloalkoxy, $(C_{6-14})$-aryl, $(C_{5-14})$-heteroaryl, $(C_{6-14})$-aryloxy, $(C_{5-14})$-heteroaryloxy, $(C_{1-20})$-alk-$(C_{6-14})$-aryl, $(C_{1-20})$-alk-$(C_{5-14})$-heteroaryl, $(C_{1-20})$-alk-$(C_{6-14})$-aryloxy, $(C_{1-20})$-alk-$(C_{5-14})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' and n is 0-3; R is H, $(C_{1-20})$-alkyl, $(C_{6-14})$-aryl or $(C_{5-14})$-heteroaryl; R' is H, $(C_{1-20})$-alkyl, $(C_{3-10})$-cycloalkyl, $(C_{6-14})$-aryl or $(C_{5-14})$-heteroaryl;

Y is O or NR" and each R" independently represents H, $(C_{1-20})$-alkyl, $(C_{3-10})$-cycloalkyl, $(C_{6-14})$-aryl, $(C_{5-14})$-heteroaryl or $(C_{1-20})$-alkanoyl;

$R_5$ is H, $(C_{1-20})$-alkyl or $(C_{3-10})$-cycloalkyl;

$R_6$, $R_7$ together represent a cis double bond or —O— or each of $R_6$ and $R_7$ independently represents H or OR'" and each R'" independently represents H, $(C_{1-20})$-alkyl, $(C_{3-10})$-cycloalkyl, $(C_{6-14})$-aryl, $(C_{5-14})$-heteroaryl or $(C_{1-20})$-alkanoyl;

$R_8$, $R_9$ together represent a double bond or —O— or each of $R_8$ and $R_9$ independently represents H or OR'" and each R'" independently represents H, $(C_{1-20})$-alkyl, $(C_{3-10})$-cycloalkyl, $(C_{6-14})$-aryl, $(C_{5-14})$-heteroaryl or $(C_{1-20})$-alkanoyl;

$R_{10}$, $R_{11}$ together represent a double bond or —O— or each of $R_{10}$ and $R_{11}$ independently represents H or OR'" and each R'" independently represents H, $(C_{1-20})$-alkyl, $(C_{3-10})$-cycloalkyl, $(C_{6-14})$-aryl, $(C_{5-14})$-heteroaryl or $(C_{1-20})$-alkanoyl; and Z is O, S, —OR'" or —SR'"; and each R'" independently represents H, $(C_{1-20})$-alkyl, $(C_{3-10})$-cycloalkyl, $(C_{6-14})$-aryl, $(C_{5-14})$-heteroaryl or $(C_{1-20})$-alkanoyl.

In another embodiment, the $R_1$, $R_3$ are each independently H, $(C_{1-10})$-alkyl, $(C_{3-7})$-cycloalkyl, $(C_{6-10})$-aryl, $(C_{5-10})$-heteroaryl or $(C_{1-10})$-alkanoyl. In another embodiment, $R_1$, $R_3$ are each independently H, $(C_{1-7})$-alkyl, $(C_{3-7})$-cycloalkyl, $(C_6)$-aryl, $(C_{5-6})$-heteroaryl or $(C_{1-7})$-alkanoyl. In another embodiment, $R_1$, $R_3$ are each independently H, $(C_{1-4})$-alkyl, $(C_{3-6})$-cycloalkyl, $(C_6)$-aryl, $(C_{5-6})$-heteroaryl or $(C_{1-4})$-alkanoyl. In another embodiment, $R_1$, $R_3$ are H or methyl.

In another embodiment, $R_2$, $R_4$ are each independently selected from the group consisting of H, $(C_{1-10})$-alkyl, $(C_{3-7})$-cycloalkyl, $(C_{1-10})$-alkoxy, $(C_{3-7})$-cycloalkoxy, $(C_{6-10})$-aryl, $(C_{5-10})$-heteroaryl, $(C_{6-10})$-aryloxy, $(C_{5-10})$-heteroaryloxy, $(C_{1-10})$-alk-$(C_{6-10})$-aryl, $(C_{1-10})$-alk-$(C_{5-10})$-heteroaryl, $(C_{1-10})$-alk-$(C_{6-10})$-aryloxy, $(C_{1-10})$-alk-$(C_{5-10})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' and n is 0-3; R is H, $(C_{1-10})$-alkyl, $(C_{3-7})$-cycloalkyl, $(C_{6-10})$-aryl or $(C_{5-10})$-heteroaryl; R' is H, $(C_{1-10})$-alkyl, $(C_{3-7})$-cycloalkyl, $(C_{6-10})$-aryl or $(C_{5-10})$-heteroaryl. In another embodiment, $R_2$, $R_4$ are each independently selected from the group consisting of H, $(C_{1-7})$-alkyl, $(C_{3-6})$-cycloalkyl, $(C_{1-7})$-alkoxy, $(C_{3-6})$-cycloalkoxy, $(C_6)$- aryl, $(C_{5-6})$-heteroaryl, $(C_6)$-aryloxy, $(C_{5-6})$-heteroaryloxy, $(C_{1-7})$-alk-$(C_6)$-aryl, $(C_{1-7})$-alk-$(C_{5-6})$-heteroaryl, $(C_{1-7})$-alk-$(C_6)$-aryloxy, $(C_{1-7})$-alk-$(C_{5-6})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' and n is 0-3; R is H, $(C_{1-7})$-alkyl, $(C_{3-6})$-cycloalkyl, $(C_6)$-aryl or $(C_{5-6})$-heteroaryl; R' is H, $(C_{1-7})$-alkyl, $(C_{3-6})$-cycloalkyl, $(C_6)$-aryl or $(C_{5-6})$-heteroaryl. In another embodiment, $R_2$, $R_4$ are each independently selected from the group consisting of H, $(C_{1-4})$-alkyl, $(C_{3-6})$-cycloalkyl, $(C_{1-4})$-alkoxy, $(C_{3-6})$-cycloalkoxy, $(C_6)$-aryl, $(C_{5-6})$-heteroaryl, $(C_6)$-aryloxy, $(C_{5-6})$-heteroaryloxy, $(C_{1-4})$-alk-$(C_6)$-aryl, $(C_{1-4})$-alk-$(C_{5-6})$-heteroaryl, $(C_{1-4})$-alk-$(C_6)$-aryloxy, $(C_{1-4})$-alk-$(C_{5-6})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR' and n is 0-3; R is H, $(C_{1-4})$-alkyl, $(C_{3-6})$-cycloalkyl, $(C_6)$-aryl or $(C_{5-6})$-heteroaryl; R' is H, $(C_{1-4})$-alkyl, $(C_{3-6})$-cycloalkyl, $(C_6)$-aryl or $(C_{5-6})$-heteroaryl. In one embodiment, $R_2$, $R_4$ are each H.

In another embodiment, Y is O or NR" and each R" independently represents H, $(C_{1-10})$-alkyl, $(C_{3-7})$-cycloalkyl, $(C_{6-10})$-aryl, $(C_{5-10})$-heteroaryl or $(C_{1-10})$-alkanoyl. In another embodiment, Y is O or NR" and each R" independently represents H, $(C_{1-7})$-alkyl, $(C_{3-6})$-cycloalkyl, $(C_6)$-aryl, $(C_{5-6})$-heteroaryl or $(C_{1-7})$-alkanoyl. In another embodiment, Y is O or NR" and each R" independently represents H, $(C_{1-4})$-alkyl, $(C_{3-6})$-cycloalkyl, $(C_6)$-aryl, $(C_{5-6})$-heteroaryl or $(C_{1-4})$-alkanoyl. In another embodiment, Y is O.

In another embodiment, $R_5$ is H or $(C_{1-10})$-alkyl or $(C_{3-7})$-cycloalkyl. In another embodiment, $R_5$ is H or $(C_{1-7})$-alkyl or $(C_{3-6})$-cycloalkyl. In another embodiment, $R_5$ is H or $(C_{1-4})$-alkyl. In another embodiment, $R_5$ is methyl.

In another embodiment, $R_6$, $R_7$ together represent a cis double bond or —O— or each of $R_6$ and $R_7$ independently represents H or OR'" and each R'" independently represents H, $(C_{1-10})$-alkyl, $(C_{3-7})$-cycloalkyl, $(C_{6-10})$-aryl, $(C_{5-10})$-heteroaryl or $(C_{1-10})$-alkanoyl. In another embodiment, $R_6$, $R_7$ together represent a cis double bond or —O— or each of $R_6$ and $R_7$ independently represents H or OR'" and each R'" independently represents H, $(C_{1-7})$-alkyl, $(C_{3-6})$-cycloalkyl, $(C_6)$-aryl, $(C_{5-6})$-heteroaryl or $(C_{1-7})$-alkanoyl. In another embodiment, $R_6$, $R_7$ together represent a cis double bond or —O— or each of $R_6$ and $R_7$ independently represents H or OR'" and each R'" independently represents H, $(C_{1-4})$-alkyl, $(C_{3-6})$-cycloalkyl, $(C_6)$-aryl, $(C_{5-6})$-heteroaryl or $(C_{1-4})$-alkanoyl. In one embodiment, $R_6$, $R_7$ together represent a cis double bond.

In another embodiment, $R_8$, $R_9$ together represent a double bond or —O— or each of $R_8$ and $R_9$ independently represents H or OR'" and each R'" independently represents H, $(C_{1-10})$-alkyl, $(C_{3-7})$-cycloalkyl, $(C_{6-10})$-aryl, $(C_{5-10})$-heteroaryl or $(C_{1-10})$-alkanoyl. In another embodiment, $R_8$, $R_9$ together represent a double bond or —O— or each of $R_8$ and $R_9$ independently represents H or OR'" and each R'" independently represents H, $(C_{1-7})$-alkyl, $(C_{3-6})$-cycloalkyl, $(C_6)$-aryl, $(C_{5-6})$-heteroaryl or $(C_{1-7})$-alkanoyl. In another embodiment, $R_8$, $R_9$ together represent a double bond or —O— or each of $R_8$ and $R_9$ independently represents H or OR'" and each R'" independently represents H, $(C_{1-4})$-alkyl, $(C_{3-6})$-cycloalkyl, $(C_6)$-aryl, $(C_{5-6})$-heteroaryl or $(C_{1-4})$-alkanoyl. In another embodiment, each of $R_8$ and $R_9$ independently represents OR'" and each R'" independently represents H.

In another embodiment, $R_{10}$, $R_{11}$ together represent a double bond or —O— or each of $R_{10}$ and $R_{11}$ independently represents H or OR'" and each R'" independently represents H, $(C_{1-10})$-alkyl, $(C_{3-7})$-cycloalkyl, $(C_{6-10})$-aryl, $(C_{5-10})$-heteroaryl or $(C_{1-10})$-alkanoyl. In another embodiment, $R_{10}$, $R_{11}$ together represent a double bond or —O— or each of $R_{10}$ and $R_{11}$ independently represents H or OR'" and each R'" independently represents H, $(C_{1-7})$-alkyl, $(C_{3-6})$-cycloalkyl, $(C_6)$-aryl, $(C_{5-6})$-heteroaryl or $(C_{1-7})$-alkanoyl. In another embodiment, $R_{10}$, $R_{11}$ together represent a double bond or —O— or each of $R_{10}$ and $R_{11}$ independently represents H or OR'" and each R'" independently represents H, $(C_{1-4})$-alkyl, $(C_{3-6})$-cycloalkyl, $(C_6)$-aryl, $(C_{5-6})$-heteroaryl or $(C_{1-4})$-alkanoyl. In another embodiment, $R_{10}$, $R_{11}$ together represent a double bond.

In another embodiment, Z is O, S, —OR'" or —SR'"; and each R'" independently represents H, $(C_{1-10})$-alkyl, $(C_{3-7})$-cycloalkyl, $(C_{6-10})$-aryl, $(C_{5-10})$-heteroaryl or $(C_{1-10})$-alkanoyl. In another embodiment, Z is O, S, —OR'" or —SR'"; and each R'" independently represents H, $(C_{1-7})$-alkyl, $(C_{3-6})$-cycloalkyl, $(C_6)$-aryl, $(C_{5-6})$-heteroaryl or $(C_{1-7})$-alkanoyl. In another embodiment, Z is O, S, —OR'" or —SR'"; and each R'" independently represents H, $(C_{1-4})$-alkyl, $(C_{3-6})$-cycloalkyl, $(C_6)$-aryl, $(C_{5-6})$-heteroaryl or $(C_{1-4})$-alkanoyl. In another embodiment, Z is O.

One example of a RAL is LL-Z1640-2 (also known as (5Z)-7-oxozeaenol, C292, FR148083 or f152A1) that was first reported in 1978[42]. It was identified in 2003 in a screen for TAK1 inhibition[40]. This compound is competitive with ATP and irreversibly inhibits TAK1. TAK1 is a MAPKKK involved in the JNK/p38 signalling cascade for proinflammation signals such as cytokines. The authors also demonstrated LL-Z1640-2 to effectively prevent inflammation in an animal model (topical application). LL-Z1640-2 was recently reported to inhibit ERK2 enzyme activity and subsequent TGFβ-induced AP-1 activation[43]. In addition, an X-ray crystal structure of the ERK2/LL-Z1640-2 complex and structure-activity relationships (SAR) indicated that both the cis-enone and the conformation of the 14-membered resorcylic acid lactone ring contribute to this inhibitory activity. This structure revealed that the compound binds to the ATP binding site of ERK2, involving a covalent bond to Sy of ERK2 Cys166. The authors concluded that covalent binding to the common cysteine residue in the ATP-binding site is likely to play a crucial role in the inhibitory activity against MAP kinases. Therefore, a useful compound of formula (I) is (3S,5Z,8S,9S,11E)-3,4,9,10-tetrahydro-8,9,16-trihydroxy-14-methoxy-3-methyl-1H-2-benzoxacyclotetradecin-1,7(8H)-dione (i.e. (5Z)-7-oxozeaenol) represented by formula (II) below:

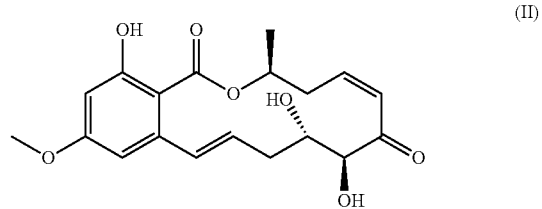 [SMILES: COc1cc(O)c2c(c1)/C=C/C[C@H](O)[C@H](O)C(=O)/C=C\C[C@H](C)OC2=O]

(II)

In another illustrative embodiment, the indolinone-containing compound has the formula (III) below including all stereoisomers, polymorphs, metabolites and pharmaceutically acceptable derivatives such as, but not limited to, pharmaceutically acceptable salts, esters, hydrates, prodrugs, solvates or combinations thereof:

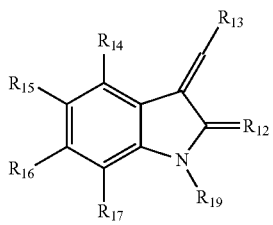

(III)

wherein $R_{12}$ is O, S, —OR''' or —SR'''; and each R''' independently represents R is H, alkyl, cycloalkyl, aryl, heteroaryl or alkanoyl (when $R_{12}$ is —OR''' or —SR''' it will be understood that the carbon atom attached to $R_{12}$ is also bonded to a hydrogen);

$R_{13}$ is a five membered nitrogen containing heterocyclic aromatic ring, optionally substituted with one or more substituents independently selected from the group consisting of alkyl, cycloalkyl, alkoxy, cycloalkoxy, aryl, heteroaryl, aryloxy, heteroaryloxy, alkaryl, alkheteroaryl, alkaryloxy, alkheteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, alkyl, cycloalkyl, aryl or heteroaryl; and R' is H, alkyl, cycloalkyl, aryl or heteroaryl;

$R_{14}$, $R_{15}$, $R_{16}$, and $R_{17}$ are each independently selected from the group consisting of H, alkyl, cycloalkyl, alkoxy, cycloalkoxy, aryl, heteroaryl, aryloxy, heteroaryloxy, alkaryl, alkheteroaryl, alkaryloxy, alkheteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$, and CONRR'; and n is 0-3; R is H, alkyl, cycloalkyl, aryl or heteroaryl; and R' is H, alkyl, cycloalkyl, aryl or heteroaryl; and $R_{19}$ is H, alkyl or cycloalkyl.

In another embodiment, the compound of the formula (III) has the following definitions:

$R_{12}$ is O, S, —OR''' or —SR'''; and each R''' independently represents H, $(C_{1-20})$-alkyl, $(C_{3-10})$-cycloalkyl, $(C_{6-14})$-aryl, $(C_{5-14})$-heteroaryl or $(C_{1-20})$-alkanoyl;

$R_{13}$ is a five membered nitrogen containing heterocyclic aromatic ring, optionally substituted with one or more substituents independently selected from the group consisting of $(C_{1-20})$-alkyl, $(C_{3-10})$-cycloalkyl, $(C_{1-20})$-alkoxy, $(C_{3-10})$-cycloalkoxy, $(C_{6-14})$-aryl, $(C_{5-14})$-heteroaryl, $(C_{6-14})$-aryloxy, $(C_{5-14})$-heteroaryloxy, $(C_{1-20})$-alk-$(C_{6-14})$-aryl, $(C_{1-20})$-alk-$(C_{5-14})$-heteroaryl, $(C_{1-20})$-alk-$(C_{6-14})$-aryloxy, $(C_{1-20})$-alk-$(C_{5-14})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, $(C_{1-20})$-alkyl, $(C_{6-14})$-aryl or $(C_{5-14})$-heteroaryl; R' is H, $(C_{1-20})$-alkyl, $(C_{3-10})$-cycloalkyl, $(C_{6-14})$-aryl or $(C_{5-14})$-heteroaryl;

$R_{14}$, $R_{15}$, $R_{16}$, and $R_{17}$ are each independently selected from the group consisting of H, $(C_{1-20})$-alkyl, $(C_{3-10})$-cycloalkyl, $(C_{1-20})$-alkoxy, $(C_{3-10})$-cycloalkoxy, $(C_{6-14})$-aryl, $(C_{5-14})$-heteroaryl, $(C_{6-14})$-aryloxy, $(C_{5-14})$-heteroaryloxy, $(C_{1-20})$-alk-$(C_{6-14})$-aryl, $(C_{1-20})$-alk-$(C_{5-14})$-heteroaryl, $(C_{1-20})$-alk-$(C_{6-14})$-aryloxy, $(C_{1-20})$-alk-$(C_{5-14})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)CO_2R$ and CONRR'; and n is 0-3; R is H, $(C_{1-20})$-alkyl, $(C_{6-14})$-aryl or $(C_{5-14})$-heteroaryl; R' is H, $(C_{1-20})$-alkyl, $(C_{3-10})$-cycloalkyl, $(C_{6-14})$-aryl or $(C_{5-14})$-heteroaryl; and $R_{19}$ is H, $(C_{1-20})$-alkyl, $(C_{3-10})$-cycloalkyl.

In another embodiment, $R_{12}$ is O, S, —OR''' or —SR'''; and each R''' independently represents H, $(C_{1-10})$-alkyl, $(C_{3-7})$-cycloalkyl, $(C_{6-10})$-aryl, $(C_{5-10})$-heteroaryl or $(C_{1-10})$-alkanoyl. In another embodiment, $R_{12}$ is O, S, —OR''' or —SR'''; and each R''' independently represents H, $(C_{1-7})$-alkyl, $(C_{3-6})$-cycloalkyl, $(C_6)$-aryl, $(C_{5-6})$-heteroaryl or $(C_{1-7})$-alkanoyl. In another embodiment, $R_{12}$ is O, S, —OR''' or —SR'''; and each R''' independently represents H, $(C_{1-4})$-alkyl, $(C_{3-6})$-cycloalkyl, $(C_6)$-aryl, $(C_{5-6})$-heteroaryl or $(C_{1-4})$-alkanoyl. In another embodiment, $R_{12}$ is O.

In another embodiment, $R_{13}$ is a five membered nitrogen containing heterocyclic aromatic ring, optionally substituted with one or more substituents independently selected from the group consisting of $(C_{1-10})$-alkyl, $(C_{3-7})$-cycloalkyl, $(C_{1-10})$-alkoxy, $(C_{3-7})$-cycloalkoxy, $(C_{6-10})$-aryl, $(C_{5-10})$-heteroaryl, $(C_{6-10})$-aryloxy, $(C_{5-10})$-heteroaryloxy, $(C_{1-10})$-alk-$(C_{6-10})$-aryl, $(C_{1-10})$-alk-$(C_{5-10})$-heteroaryl, $(C_{1-10})$-alk-$(C_{6-10})$-aryloxy, $(C_{1-10})$-alk-$(C_{5-10})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, $(C_{1-10})$-alkyl, $(C_{3-7})$-cycloalkyl, $(C_{6-10})$-aryl or $(C_{5-10})$-heteroaryl; R' is H, $(C_{1-10})$-alkyl, $(C_{3-7})$-cycloalkyl, $(C_{6-10})$-aryl or $(C_{5-10})$-heteroaryl. In another embodiment, $R_{13}$ is a five membered nitrogen containing heterocyclic aromatic ring, optionally substituted with one or more substituents independently selected from the group consisting of $(C_{1-7})$-alkyl, $(C_{3-6})$-cycloalkyl, $(C_{1-7})$-alkoxy, $(C_{3-6})$-cycloalkoxy, $(C_6)$-aryl, $(C_{5-6})$-heteroaryl, $(C_6)$-aryloxy, $(C_{5-6})$-heteroaryloxy, $(C_{1-7})$-alk-$(C_6)$-aryl, $(C_{1-7})$-alk-$(C_{5-6})$-heteroaryl, $(C_{1-7})$-alk-$(C_6)$-aryloxy, $(C_{1-7})$-alk-$(C_{5-6})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, $(C_{1-7})$-alkyl, $(C_{3-6})$-cycloalkyl, $(C_6)$-aryl or $(C_{5-6})$-heteroaryl; R' is H, $(C_{1-7})$-alkyl, $(C_{3-6})$-cycloalkyl, $(C_6)$-aryl or $(C_{5-6})$-heteroaryl. In another embodiment, $R_{13}$ is a five membered nitrogen containing heterocyclic aromatic ring, optionally substituted with one or more substituents independently selected from the group consisting of $(C_{1-4})$-alkyl, $(C_{3-6})$-cycloalkyl, $(C_{1-4})$-alkoxy, $(C_{3-6})$-cycloalkoxy, $(C_6)$-aryl, $(C_{5-6})$-heteroaryl, $(C_6)$-aryloxy, $(C_{5-6})$-heteroaryloxy, $(C_{1-4})$-alk-$(C_6)$-aryl, $(C_{1-4})$-alk-$(C_{5-6})$-heteroaryl, $(C_{1-4})$-alk-$(C_6)$-aryloxy, $(C_{1-4})$-alk-$(C_{5-6})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, $(C_{1-4})$-alkyl, $(C_{3-6})$-cycloalkyl, $(C_6)$-aryl or $(C_{5-6})$-heteroaryl; R' is H, $(C_{1-4})$-alkyl, $(C_{3-6})$-cycloalkyl, $(C_6)$-aryl or $(C_{5-6})$-heteroaryl. In another embodiment, $R_{13}$ is optionally substituted pyrrole. In another embodiment, the optional substituents on the five membered nitrogen containing heterocyclic aromatic ring are methyl or —$(CH_2)_2CO_2H$. In another embodiment, $R_{13}$ is

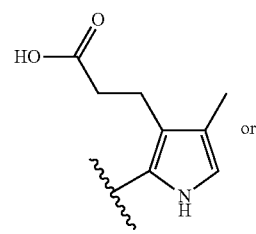

or

-continued

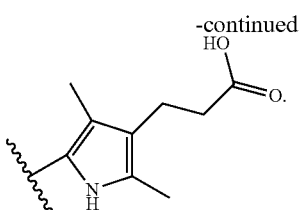

In another embodiment, $R_{14}$, $R_{15}$, $R_{16}$, and $R_{17}$ are each independently selected from the group consisting of H, $(C_{1-10})$-alkyl, $(C_{3-7})$-cycloalkyl, $(C_{1-10})$-alkoxy, $(C_{3-7})$-cycloalkoxy, $(C_{6-10})$-aryl, $(C_{5-10})$-heteroaryl, $(C_{6-10})$-aryloxy, $(C_{5-10})$-heteroaryloxy, $(C_{1-10})$-alk-$(C_{6-10})$-aryl, $(C_{1-10})$-alk-$(C_{5-10})$-heteroaryl, $(C_{1-10})$-alk-$(C_{6-10})$-aryloxy, $(C_{1-10})$-alk-$(C_{5-10})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, $(C_{1-10})$-alkyl, $(C_{3-7})$-cycloalkyl, $(C_{6-10})$-aryl or $(C_{5-10})$-heteroaryl; R' is H, $(C_{1-10})$-alkyl, $(C_{3-7})$-cycloalkyl, $(C_{6-10})$-aryl or $(C_{5-10})$-heteroaryl. In another embodiment, $R_{14}$, $R_{15}$, $R_{16}$, and $R_{17}$ are each independently selected from the group consisting of H, $(C_{1-7})$-alkyl, $(C_{3-6})$-cycloalkyl, $(C_{1-7})$-alkoxy, $(C_{3-6})$-cycloalkoxy, $(C_6)$-aryl, $(C_{5-6})$-heteroaryl, $(C_6)$-aryloxy, $(C_{5-6})$-heteroaryloxy, $(C_{1-7})$-alk-$(C_6)$-aryl, $(C_{1-7})$-alk-$(C_{5-6})$-heteroaryl, $(C_{1-7})$-alk-$(C_6)$-aryloxy, $(C_{1-7})$-alk-$(C_{5-6})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, $(C_{1-7})$-alkyl, $(C_{3-6})$-cycloalkyl, $(C_6)$-aryl or $(C_{5-6})$-heteroaryl; R' is H, $(C_{1-7})$-alkyl, $(C_{3-6})$-cycloalkyl, $(C_6)$-aryl or $(C_{5-6})$-heteroaryl. In another embodiment, $R_{14}$, $R_{15}$, $R_{16}$, and $R_{17}$ are each independently selected from the group consisting of H, $(C_{1-4})$-alkyl, $(C_{3-6})$-cycloalkyl, $(C_{1-4})$-alkoxy, $(C_{3-6})$-cycloalkoxy, $(C_6)$-aryl, $(C_{5-6})$-heteroaryl, $(C_6)$-aryloxy, $(C_{5-6})$-heteroaryloxy, $(C_{1-4})$-alk-$(C_6)$-aryl, $(C_{1-4})$-alk-$(C_{5-6})$-heteroaryl, $(C_{1-4})$-alk-$(C_6)$-aryloxy, $(C_{1-4})$-alk-$(C_{5-6})$-heteroaryloxy, halogen, trihalomethyl, S(O)R, $SO_2NRR'$, $SO_3R$, SR, $NO_2$, NRR', OH, CN, C(O)R, OC(O)R, NHC(O)R, $(CH_2)_nCO_2R$ and CONRR'; and n is 0-3; R is H, $(C_{1-4})$-alkyl, $(C_{3-6})$-cycloalkyl, $(C_6)$-aryl or $(C_{5-6})$-heteroaryl; R' is H, $(C_{1-4})$-alkyl, $(C_{3-6})$-cycloalkyl, $(C_6)$-aryl or $(C_{5-6})$-heteroaryl. In another embodiment, $R_{14}$, $R_{15}$, $R_{16}$, and $R_{17}$ are each H.

In another embodiment, $R_{19}$ is H, $(C_{1-10})$-alkyl, $(C_{3-7})$-cycloalkyl. In another embodiment, $R_{19}$ is H, $(C_{1-7})$-alkyl, $(C_{3-6})$-cycloalkyl. In another embodiment, $R_{19}$ is H, $(C_{1-4})$-alkyl, $(C_{3-6})$-cycloalkyl. In another embodiment, $R_{19}$ is H.

Compounds of Formula III are optionally prepared according to methods set out in U.S. Pat. No. 6,906,093.

One example of an indolinone-containing compound is SU5402 which is a known inhibitor of the receptor tyrosine kinases such as Fibroblast Growth Factor Receptors (FGFRs), Vascular Endothelial Growth Factor Receptors (VEGFRs) and Platelet Derived Growth Factor Receptors (PDGFRs)[44,45]. Precisely controlled FGF-derived signals are key components in the regulation of vertebrate development during embryogenesis and also at later stages during growth and differentiation of various tissues and organs[46]. FGFs act as mitogens and some members induce cell migration, angiogenesis, neurite outgrowth, and cell survival[47]. Strong indications for an important role of FGF/FGFR signals in malignant growth and probably malignant transformation have been published for several epithelial solid tumors including prostate, bladder, kidney, and breast cancer[48,49]. VEGFRs are receptor tyrosine kinases for members of the Vascular Endothelial Growth Factor family (VEGFs). VEGFs are important signaling proteins involved in both vasculogenesis and angiogenesis. The VEGF signaling pathway appears to be the dominant pathway involved in the development of pathological angiogenesis and therefore of disease states such as cancer, psoriasis, rheumatoid arthritis, chronic inflammation and diabetic retinopathy[50-58]. Platelet-derived growth factors (PDGFs) and their tyrosine kinase receptors (PDGFRs) play an important role in angiogenesis, embryonic (e.g. gastrulation) and postnatal development, organogenesis (e.g. lung, intestine, skin, testis, kidney, lens), and are implicated in the wide variety of malignancies[59-63]. Furthermore, PDGFs drive responses in vascular disorders such as atherosclerosis, pulmonary hypertension, restenosis, and retinal diseases, as well as in fibrotic diseases, including pulmonary fibrosis, scleroderma, liver cirrhosis, glomerulosclerosis, and cardiac fibrosis[59]. Therefore, a useful compound of formula (III) is 3-[4-methyl-2-[(Z)-(2-oxo-1H-indol-3-ylidene)methyl]-1H-pyrrol-3-yl]propanoic acid (i.e. SU5402) represented by formula (IV) below:

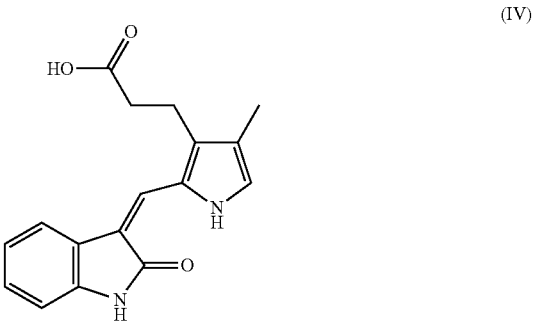 [SMILES: Cc1c[nH]c(/C=C2\C(=O)Nc3ccccc32)c1CCC(=O)O]

(IV)

Another example of an indolinone-containing compound is SU6668 (TSU-68) which is an inhibitor of Platelet Derived Growth Factor Receptors (PDGFRs), Vascular Endothelial Growth Factor Receptors (VEGFRs), Fibroblast Growth Factor Receptors (FGFRs)[44] and thus is a potent antiangiogenic and antitumor agent[64,65]. Therefore, a useful compound of formula (III) is 3-[2,4-dimethyl-5-[(Z)-(2-oxo-1H-indol-3-ylidene)methyl]-1H-pyrrol-3-yl]propanoic acid (i.e. SU6668 or TSU-68) represented by formula (V) below:

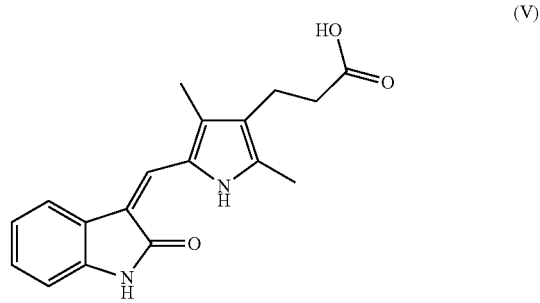 [SMILES: Cc1[nH]c(/C=C2\C(=O)Nc3ccccc32)c(C)c1CCC(=O)O]

(V)

The present disclosure therefore includes a method of treating cystic fibrosis (CF; mucoviscidosis) or other diseases associated with protein cellular processing (e.g. folding, trafficking, or post-translational modification) errors in a subject in need thereof, said method comprising administering to said subject, an effective amount of a compound of the formula I, II, III, IV and/or V, as defined above, including all stereoisomers, polymorphs, metabolites and pharmaceutically acceptable derivatives thereof and combinations thereof. In certain embodiments, the disclosure also relates to uses and methods of treatment of a subject with reduced function protein, such as reduced function CFTR (such as a class 2 CFTR mutation), by administering a compound described herein to the subject. Optionally the subject is a mammal, more typically a human. Typically the reduced function protein is due to the protein being aberrantly processed protein, meaning that the reduced function results from aberrant processing, such as errors in folding, trafficking or post-translational modification. Optionally the reduced function protein is misfolded protein (e.g. mutant protein) such as misfolded mutant CFTR (e.g. such as a class 2 CFTR mutation such as delF508-CFTR).

The disclosure also includes a use of a compound of the formula I, II, III, IV and/or V, as defined above, including all stereoisomers, polymorphs, metabolites and pharmaceutically acceptable derivatives thereof and combinations thereof, for treating cystic fibrosis (CF; mucoviscidosis) or other diseases associated with protein cellular processing (e.g. folding, trafficking, or post-translational modification) errors. The disclosure also provides use of the compounds disclosed herein for preparation of a medicament for treatment of these diseases.

Also included in the present disclosure is a compound of the formula I, II, III, IV and/or V, as defined above, including all stereoisomers, polymorphs, metabolites and pharmaceutically acceptable derivatives thereof and combinations thereof, for use in treating cystic fibrosis (CF; mucoviscidosis) or other diseases associated with protein cellular processing (e.g. folding, trafficking, or post-translational modification) errors.

The present disclosure also includes a use of a compound of the formula I, II, III, IV and/or V, as defined above, including all stereoisomers, polymorphs, metabolites and pharmaceutically acceptable derivatives thereof and combinations thereof, to prepare a medicament for treating cystic fibrosis (CF; mucoviscidosis) or other diseases associated with protein cellular processing (e.g. folding, trafficking, or post-translational modification) errors.

The present disclosure further includes a pharmaceutical composition for treating cystic fibrosis (CF; mucoviscidosis) or other diseases associated with protein cellular processing (e.g. folding, trafficking, or post-translational modification) errors comprising a compound of the formula I, II, III, IV and/or V, as defined above, including all stereoisomers, polymorphs, metabolites and pharmaceutically acceptable derivatives thereof and combinations thereof, in combination with a pharmaceutically acceptable carrier.

In certain embodiments, the invention relates to a use or method for treating a disease mediated by a misfolded form of CFTR (for example, as a result of a class mutation) in a subject in need of treatment, the method comprising administering to the subject a compound disclosed herein. The CFTR is optionally delF508-CFTR. The disclosure also provides a pharmaceutical composition useful in the treatment of a subject having a disease mediated by a misfolded form of CFTR.

The production of pharmaceutical compositions is effected in a manner which will be familiar to any person skilled in the art by bringing the described compounds of the disclosure, together with suitable, non-toxic, inert, therapeutically compatible solid, liquid or aerosol carrier materials and, if desired, usual pharmaceutical adjuvants.

Suitable carrier materials are not only inorganic carrier materials, but also organic carrier materials. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, salts for varying the osmotic pressure, buffer substances, solubilizers, colorants and antioxidants come into consideration as pharmaceutical adjuvants.

The dosage of the pharmaceutical compositions varies within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

In one embodiment, the compounds of the disclosure are formulated to be administered as compositions for oral administration in the form of gelatin capsules, tablets, SC tablets or capsules. In another embodiment, the compounds of the disclosure are formulated to be administered as compositions in the form of a solution for parenteral administration or intravenous administration (injection). In another embodiment, the compounds of the disclosure are formulated to be administered as compositions in the form of an aerosol for aerosol administration.

EXPERIMENTAL

Materials and Methods

Cell Lines

HEK293 MSR GripTite (293MSR-GT) cells stably expressing eYFP(H148Q/I152L) and delF508-CFTR protein were cultured in DMEM medium supplemented with 10% FBS, 1× Non-Essential Amino Acids, 0.6 mg/ml G418, 10 μg/ml blasticidin and 50 μg/ml zeocin at 37° C., 5% $CO_2$ in humidified atmosphere. Protein expression and rescue of delF508-CFTR were validated by immunoblotting with anti-CFTR monoclonal antibodies (clone M3A7, Chemicon Cat.#MAB3480) as described previously[66]. Baby hamster kidney (BHK) cells stably expressing delF508-CFTR mutant protein with the triple hemagglutinin (3HA) tag at the ectodomain were propagated as monolayer cultures in Dulbecco's modified Eagle's medium-F12 medium 1:1 supplemented with 5% FBS and 0.5 mM methotrexate at 37° C., 5% $CO_2$. Madin Darby Canine Kidney (MDCK) cells stably expressing delF508-CFTR protein were cultured in DMEM medium supplemented with 10% FBS, 1× PenStrep and 5 μg/ml blasticidin at 37° C., 5% $CO_2$. Before the short-circuit studies MDCK cells were grown on Snapwell inserts (Corning) for 5 days with following treatment with 10 μM (5Z)-7-oxozeaenol (Tocris), SU5402 (Tocris) or SU6668 (Tocris) for 48 hrs. Primary human bronchial epithelial cells homozygous for delF508-CFTR were provided by University of Iowa Cell Culture Facility, and propagated on collagen-coated permeable minicell inserts (Millipore) as previously described[67]. Prior to Ussing chamber assay the delF508-CFTR inserts were treated with 10 μM (5Z)-7-oxozeaenol, SU5402, SU6668 or 0.2% DMSO (negative control) for 48 hrs at 37° C.

Cellomics YFP Quenching Assay

Cellomics YFP quenching assay was performed as described previously[66]. Briefly, 50,000 293MSR-GT cells (stably expressing delF508-CFTR and eYFP(H148Q/I152L)) per well were seeded in the 96-well plates. The next day the cells were treated with 10 μM (5Z)-7-oxozeaenol, SU5402 or corr-4-a (positive control). After 48 hrs of incubation the medium was replaced with 152 µl of chloride solution (137 mM NaCl, 2.7 mM KCl, 0.7 mM CaCl$_2$, 1.1 mM MgCl$_2$, 1.5 mM KH$_2$PO$_4$, 8.1 mM Na$_2$HPO$_4$, pH 7.1), in the absence or presence of FIG (25 M Forskolin, 45 µM IBMX, 50 µM Genistein) at 37° C. After 20 min incubation, 92 µl of iodide buffer (137 mM NaI, 2.7 mM KCl, 0.7 mM CaCl$_2$, 1.1 mM MgCl$_2$, 1.5 mM KH$_2$PO$_4$, 8.1 mM Na$_2$HPO$_4$, pH 7.1) was added (final concentration 52 mM) and the decrease in fluorescence intensity over time was recorded using the Cellomics VTI (ThermoFisher), at 30° C.

Immunoblotting

The rescue of delF508-CFTR was validated by Western blotting as described previously[66]. Briefly, at 48 hrs after adding 10 µM (5Z)-7-oxozeaenol, SU5402, 0.2% DMSO (negative control) or corr-4-a (positive control) the cells were rinsed in cold PBS and lysed in lysis buffer (50 mM Hepes pH7.5, 150 mM NaCl, 1.5 mM MgCl$_2$, 1 mM EGTA, 10% glycerol (v/v), 1% Triton X-100 (v/v), 2 mM PMSF, 2×PAL inhibitors). Proteins were resolved on SDS-PAGE, transferred to nitrocellulose membranes and immunoblotted with anti-CFTR monoclonal antibodies (M3A7, 1 µg/ml) or anti-β-actin antibodies (1:10000). Membranes were washed with 5% Blotto, incubated with HRP-conjugated goat anti-mouse antibody (1:5000) and washed with PBST. Signal was detected with SuperSignal West Femto reagent.

Flow Cytometry

The rescue of delF508-CFTR was validated by Flow cytometry as described previously 66. Briefly, at 48 hrs after adding 10 µM (5Z)-7-oxozeaenol, SU5402, SU6668 or 0.2% DMSO (negative control), BHK cells were trypsinized, washed, and re-suspended in ice-cold FACS buffer (PBS supplemented with 2% FBS). To stain the cell surface, cells were incubated with anti-HA.11 monoclonal antibody (1:25, Covance Cat.#MMS-101R) or AF647-labeled goat anti-mouse antibody (1:200, Invitrogen Cat.#A21236) as a control, for 1 h at 4° C. Subsequently the cells were washed with the cold FACS buffer and incubated with AF647-conjugated goat anti-mouse antibody (1:200) at 4° C. for 1 h. They were then washed as above and re-suspended in FACS buffer with 1 µg/ml propidium iodide. The flow-cytometric analysis was performed using LSRII System (BD Biosciences). The data from 10,000 live (propidium iodide negative) cells were stored and analyzed with FlowJo v.7.6.4 software.

Short Circuit Current (Ussing Chamber) Studies

Cell inserts (12 or 6.5 mm, Millicell) or Snapwells were mounted on an Ussing chamber apparatus (Physiological Instruments) and studied under voltage clamp conditions as previously described[67-69]. Briefly, ENaC channels were inhibited with 10 µM amiloride (Sigma); non-CFTR chloride channels were blocked with 300 µM DNDS (4,4'-dinitrostilbene-2,2'-disulfonate, Sigma); CFTR currents were stimulated using 25 µM Forskolin, 25 µM IBMX and 50 µM Genistein (Sigma) and inhibited using 50 µM CFTRinh-172 (HBE cells) or 15 µM GlyH-101 (MDCK cells). Data were recorded and analyzed using Analyzer 2.1.3.

Results

Effect of (5Z)-7-Oxozeaenol, SU5402 and SU6668 on Maturation and Function of delF508-CFTR Mutant Protein.

Figure 1:
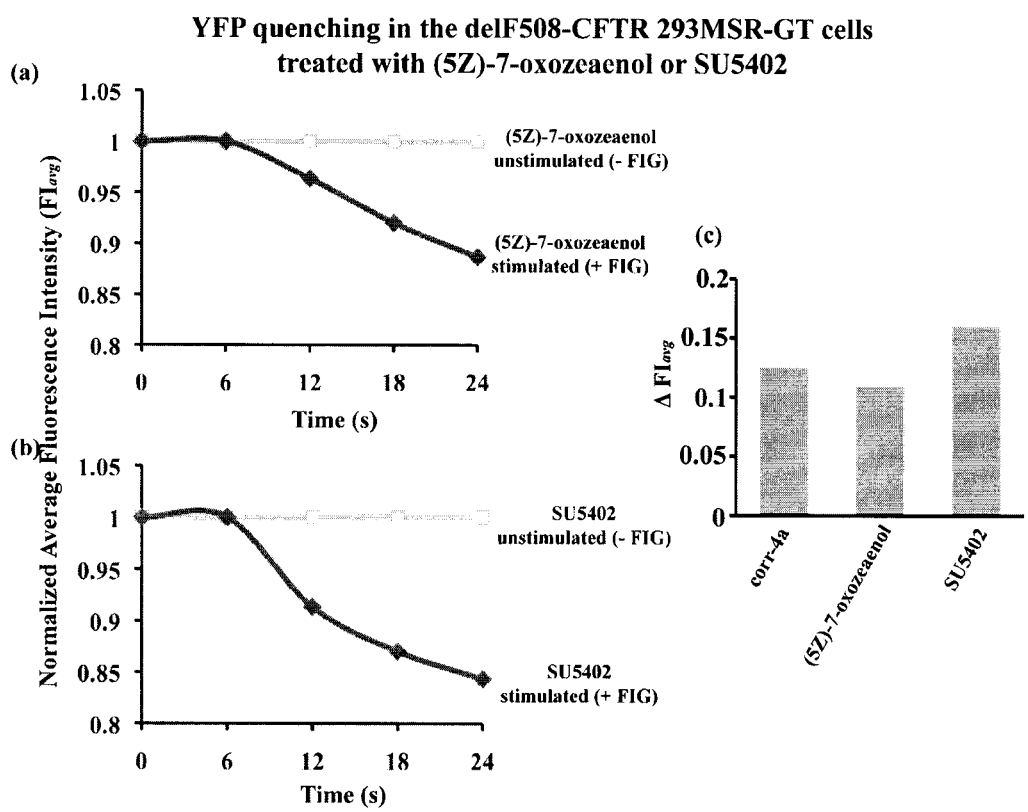
FIG. 1: Quantitative Analysis of the YFP Quenching (Cellomics) Assay.

293MSR-GT cells stably expressing eYFP(H148Q/I152L) and delF508-CFTR were treated with (5Z)-7-oxozeaenol, SU5402 or compound 4a (corr-4-a; positive control). After two days of incubation, cells were stimulated for 20 min with FIG mixture. They were then exposed to low Cl$^-$/high I$^-$ medium by replacing 137 mM Na$^+$Cl$^-$ with Na$^+$I$^-$, and fluorescence quenching of the cells due to Cl$^-$/I$^-$ exchange (presumably via CFTR) was monitored and quantified over time by the Cellomics VTI reader. FIG. 1 shows that a 48-hour treatment with (5Z)-7-oxozeaenol or SU5402 restores delF508-CFTR activity to a level that is similar to that obtained with corr-4-a. These results show that treatment of 293MSR-GT cells for 48 hrs at 37° C. with (5Z)-7-oxozeaenol or SU5402 restores trafficking to the plasma membrane of the delF508-CFTR protein and allows it to function as an ion transporter.

To further demonstrate the rescue of delF508-CFTR by the analyzed compounds, we tested for the appearance of a mature delF508-CFTR protein represented by band C in a Western (immuno) blot. DelF508-CFTR migrates primarily as a 140-150 kDa protein (band B) when analyzed by SDS-PAGE, whereas the mature wild type CFTR protein migrates primarily as a 170-180 kDa protein (band C). The differential migration of the mutant protein reflects its relative retention in the ER and failure to traffic to the Golgi where complex glycosylation is conferred to generate the mature form of the protein. As seen in FIG. 2 treatment of 293MSR-GT cells with (5Z)-7-oxozeaenol or SU5402 led to the appearance of the mature band C, similar to that seen with corr-4-a (although not as strongly as that observed following low temperature (27° C.) treatment).

As 293MSR-GT cells showed increased sensitivity toward SU6668 and we were unable to test this compound by YFP quenching assay or immunoblotting, we decided to test the appearance of delF508-CFTR protein at the plasma membrane of non-permeabilized BHK cells. BHK cells stably expressing delF508-CFTR-3HA were treated with 10 µM (5Z)-7-oxozeaenol, SU5402, SU6668, 0.2% DMSO (negative control) or grown at 27° C. (positive control) for 48 hrs. Flow cytometry was then performed on non-permeabilized cells following immunostaining for the HA epitope located at the ectodomain of delF508-CFTR, to quantify the amount of cell-surface delF508-CFTR. FIG. 3 depicts increase in cell surface expression of delF508-CFTR in the cells treated with (5Z)-7-oxozeaenol, SU5402 and SU6668 similar to that observed for the low temperature treatment.

Effect of (5Z)-7-Oxozeaenol, SU5402 and SU6668 on delF508-CFTR Trafficking and Function in MDCK Cells.

To assess CFTR chloride channel activity, a short-circuit current assay using Ussing chambers was employed on polarized epithelial MDCK monolayers stably expressing delF508-CFTR mutant protein. MDCK cells were treated with 10 µM (5Z)-7-oxozeaenol, SU5402, SU6668 or 0.2% DMSO (negative control) and grown at 37° C. for 48 hrs. The effect of compound treatment on the delF508-CFTR trafficking and function (i.e. chloride channel activity) is shown in FIG. 4.

Effect of (5Z)-7-oxozeaenol, SU5402 and SU6668 on delF508-CFTR Trafficking and Function in Primary Human Bronchial Epithelial (HBE) Cells Harvested from CF Transplant Patients.

We proceeded to investigate the consequences of (5Z)-7-oxozeaenol, SU5402 and SU6668 treatment in primary cultures of human bronchial epithelia (HBE) obtained from transplant patients homozygous for the delF508 mutation. The effect of compound treatment was compared with control (vehicle alone) on monolayers obtained from the same patient, which allowed us to eliminate the influence of patient-to-patient variability. FIGS. 5, 6 and 7 show examples from delF508/delF508 patients, where their HBE cells were treated with (5Z)-7-oxozeaenol (6 patients), SU5402 (5 patients) and SU6668 (2 patients) respectively, demonstrating enhanced activity of the mutant CFTR by (5Z)-7-oxozeaenol, SU5402 or SU6668 treatment. These findings indicate that cell surface expression of delF508-CFTR is enhanced in human bronchial epithelial cells by delivering a compound designed to correct the trafficking/maturation defect of this mutant protein, although from these latter results we cannot preclude the possibility that (5Z)-7-oxozeaenol, SU5402 and SU6668 also potentiate delF508-CFTR activity once at the plasma membrane.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1 Ratjen, F. & Doring, G. Cystic fibrosis. *Lancet* 361, 681-689 (2003).
2 Boucher, R. C., Stutts, M. J., Knowles, M. R., Cantley, L. & Gatzy, J. T. $Na^+$ transport in cystic fibrosis respiratory epithelia. Abnormal basal rate and response to adenylate cyclase activation. *J Clin Invest* 78, 1245-1252 (1986).
3 Frizzell, R. A., Halm, D. R., Rechkemmer, G. & Shoemaker, R. L. Chloride channel regulation in secretory epithelia. *Fed Proc* 45, 2727-2731 (1986).
4 Frizzell, R. A., Rechkemmer, G. & Shoemaker, R. L. Altered regulation of airway epithelial cell chloride channels in cystic fibrosis. *Science* 233, 558-560 (1986).
5 Knowles, M., Gatzy, J. & Boucher, R. Relative ion permeability of normal and cystic fibrosis nasal epithelium. *J Clin Invest* 71, 1410-1417 (1983).
6 Knowles, M. R. et al. Abnormal ion permeation through cystic fibrosis respiratory epithelium. *Science* 221, 1067-1070 (1983).
7 Knowles, M. R., Stutts, M. J., Yankaskas, J. R., Gatzy, J. T. & Boucher, R. C., Jr. Abnormal respiratory epithelial ion transport in cystic fibrosis. *Clin Chest Med* 7, 285-297 (1986).
8 Quinton, P. M. Chloride impermeability in cystic fibrosis. *Nature* 301, 421-422 (1983).
9 Quinton, P. M. Cystic fibrosis: a disease in electrolyte transport. *FASEB J* 4, 2709-2717 (1990).
10 Quinton, P. M. & Bijman, J. Higher bioelectric potentials due to decreased chloride absorption in the sweat glands of patients with cystic fibrosis. *N Engl J Med* 308, 1185-1189 (1983).
11 Collins, F. S. Cystic fibrosis: molecular biology and therapeutic implications. *Science* 256, 774-779 (1992).
12 Riordan, J. R. et al. Identification of the cystic fibrosis gene: cloning and characterization of complementary DNA. *Science* 245, 1066-1073 (1989).
13 Rommens, J. M. et al. Identification of the cystic fibrosis gene: chromosome walking and jumping. *Science* 245, 1059-1065 (1989).
14 Zielenski, J. et al. Genomic DNA sequence of the cystic fibrosis transmembrane conductance regulator (CFTR) gene. *Genomics* 10, 214-228 (1991).
15 Vankeerberghen, A., Cuppens, H. & Cassiman, J. J. The cystic fibrosis transmembrane conductance regulator: an intriguing protein with pleiotropic functions. *J Cyst Fibros* 1, 13-29 (2002).
16 Akabas, M. H. Cystic fibrosis transmembrane conductance regulator. Structure and function of an epithelial chloride channel. *J Biol Chem* 275, 3729-3732 (2000).
17 Sheppard, D. N. & Welsh, M. J. Structure and function of the CFTR chloride channel. *Physiol Rev* 79, S23-45 (1999).
18 Vergani, P., Lockless, S. W., Nairn, A. C. & Gadsby, D. C. CFTR channel opening by ATP-driven tight dimerization of its nucleotide-binding domains. *Nature* 433, 876-880 (2005).
19 Li, C., Ramjeesingh, M. & Bear, C. E. Purified cystic fibrosis transmembrane conductance regulator (CFTR) does not function as an ATP channel. *J Biol Chem* 271, 11623-11626 (1996).
20 Aleksandrov, L., Aleksandrov, A. A., Chang, X. B. & Riordan, J. R. The First Nucleotide Binding Domain of Cystic Fibrosis Transmembrane Conductance Regulator Is a Site of Stable Nucleotide Interaction, whereas the Second Is a Site of Rapid Turnover. *J Biol Chem* 277, 15419-15425 (2002).
21 Mense, M. et al. In vivo phosphorylation of CFTR promotes formation of a nucleotide-binding domain heterodimer. *EMBO J* 25, 4728-4739 (2006).
22 Kerem, B. et al. Identification of the cystic fibrosis gene: genetic analysis. *Science* 245, 1073-1080 (1989).
23 Yang, Y. et al. Molecular basis of defective anion transport in L cells expressing recombinant forms of CFTR. *Hum Mol Genet* 2, 1253-1261 (1993).
24 Yang, Y., Janich, S., Cohn, J. A. & Wilson, J. M. The common variant of cystic fibrosis transmembrane conductance regulator is recognized by hsp70 and degraded in a pre-Golgi nonlysosomal compartment. *Proc Natl Acad Sci USA* 90, 9480-9484 (1993).
25 Zhang, F., Kartner, N. & Lukacs, G. L. Limited proteolysis as a probe for arrested conformational maturation of delta F508 CFTR. *Nat Struct Biol* 5, 180-183 (1998).
26 Galietta, L. J. et al. Novel CFTR chloride channel activators identified by screening of combinatorial libraries based on flavone and benzoquinolizinium lead compounds. *J Biol Chem* 276, 19723-19728 (2001).
27 Ma, T. et al. Thiazolidinone CFTR inhibitor identified by high-throughput screening blocks cholera toxin-induced intestinal fluid secretion. *J Clin Invest* 110, 1651-1658 (2002).
28 Ma, T. et al. High-affinity activators of cystic fibrosis transmembrane conductance regulator (CFTR) chloride conductance identified by high-throughput screening. *J Biol Chem* 277, 37235-37241 (2002).
29 Pedemonte, N. et al. Small-molecule correctors of defective DeltaF508-CFTR cellular processing identified by high-throughput screening. *J Clin Invest* 115, 2564-2571 (2005).
30 Yang, H. et al. Nanomolar affinity small molecule correctors of defective Delta F508-CFTR chloride channel gating. *J Biol Chem* 278, 35079-35085 (2003).
31 Carlile, G. W. et al. Correctors of protein trafficking defects identified by a novel high-throughput screening assay. *Chembiochem* 8, 1012-1020 (2007).
32 Robert, R. et al. Structural analog of sildenafil identified as a novel corrector of the F508del-CFTR trafficking defect. *Mol Pharmacol* 73, 478-489 (2008).
33 Loo, T. W., Bartlett, M. C. & Clarke, D. M. Rescue of DeltaF508 and other misprocessed CFTR mutants by a novel quinazoline compound. *Mol Pharm* 2, 407-413 (2005).

34 Van Goor, F. et al. Rescue of DeltaF508-CFTR trafficking and gating in human cystic fibrosis airway primary cultures by small molecules. *Am J Physiol Lung Cell Mol Physiol* 290, L1117-1130 (2006).

35 C. Ansel, H., G. Popovich, N. & V. Allen, L. Pharmaceutical dosage forms and drug delivery systems (1995).

36 Aridor, M. & Hannan, L. A. Traffic jam: a compendium of human diseases that affect intracellular transport processes. *Traffic* 1, 836-851 (2000).

37 Aridor, M. & Hannan, L. A. Traffic jams II: an update of diseases of intracellular transport. *Traffic* 3, 781-790 (2002).

38 Du, H. et al. Discovery of a potent, metabolically stabilized resorcylic lactone as an anti-inflammatory lead. *Bioorg Med Chem Lett* 19, 6196-6199 (2009).

39 Fischer, H. et al. Fibroblast growth factor receptor-mediated signals contribute to the malignant phenotype of non-small cell lung cancer cells: therapeutic implications and synergism with epidermal growth factor receptor inhibition. *Mol Cancer Ther* 7, 3408-3419 (2008).

40 Ninomiya-Tsuji, J. et al. A resorcylic acid lactone, 5Z-7-oxozeaenol, prevents inflammation by inhibiting the catalytic activity of TAK1 MAPK kinase kinase. *J Biol Chem* 278, 18485-18490 (2003).

41 Winssinger, N. & Barluenga, S. Chemistry and biology of resorcylic acid lactones. *Chem Commun (Camb)*, 22-36 (2007).

42 Ellestad, G. A., Lovell, F. M., Perkinson, N. A., Hargreaves, R. T. & McGahren, W. J. New zearalenone related macrolides and isocoumarins from an unidentified fungus. *The Journal of Organic Chemistry* 43, 2339-2343 (1978).

43 Ohori, M. et al. Role of a cysteine residue in the active site of ERK and the MAPKK family. *Biochem Biophys Res Commun* 353, 633-637 (2007).

44 Sun, L. et al. Design, synthesis, and evaluations of substituted 3-[(3- or 4-carboxyethylpyrrol-2-yl)methylidenyl] indolin-2-ones as inhibitors of VEGF, FGF, and PDGF receptor tyrosine kinases. *J Med Chem* 42, 5120-5130 (1999).

45 Mohammadi, M. et al. Structures of the tyrosine kinase domain of fibroblast growth factor receptor in complex with inhibitors. *Science* 276, 955-960 (1997).

46 Ornitz, D. M. & Itoh, N. Fibroblast growth factors. *Genome Biol* 2, REVIEWS3005 (2001).

47 Powers, C. J., McLeskey, S. W. & Wellstein, A. Fibroblast growth factors, their receptors and signaling. *Endocr Relat Cancer* 7, 165-197 (2000).

48 Jeffers, M., LaRochelle, W. J. & Lichenstein, H. S. Fibroblast growth factors in cancer: therapeutic possibilities. *Expert Opin Ther Targets* 6, 469-482 (2002).

49 Cronauer, M. V., Schulz, W. A., Seifert, H. H., Ackermann, R. & Burchardt, M. Fibroblast growth factors and their receptors in urological cancers: basic research and clinical implications. *Eur Urol* 43, 309-319 (2003).

50 Argyriou, A. A., Giannopoulou, E. & Kalofonos, H. P. Angiogenesis and anti-angiogenic molecularly targeted therapies in malignant gliomas. *Oncology* 77, 1-11 (2009).

51 Backer, M. V., Hamby, C. V. & Backer, J. M. Inhibition of vascular endothelial growth factor receptor signaling in angiogenic tumor vasculature. *Adv Genet.* 67, 1-27 (2009).

52 Bhargava, P. & Robinson, M. O. Development of second-generation VEGFR tyrosine kinase inhibitors: current status. *Curr Oncol Rep* 13, 103-111 (2011).

53 Grunewald, F. S., Prota, A. E., Giese, A. & Ballmer-Hofer, K. Structure-function analysis of VEGF receptor activation and the role of coreceptors in angiogenic signaling. *Biochim Biophys Acta* 1804, 567-580 (2010).

54 Kiselyov, A., Balakin, K. V. & Tkachenko, S. E. VEGF/VEGFR signalling as a target for inhibiting angiogenesis. *Expert Opin Investig Drugs* 16, 83-107 (2007).

55 Mironidou-Tzouveleki, M., Tsartsalis, S. & Tomos, C. Vascular endothelial growth factor (VEGF) in the pathogenesis of diabetic nephropathy of type 1 diabetes mellitus. *Curr Drug Targets* 12, 107-114 (2011).

56 Olsson, A. K., Dimberg, A., Kreuger, J. & Claesson-Welsh, L. VEGF receptor signalling—in control of vascular function. *Nat Rev Mol Cell Biol* 7, 359-371 (2006).

57 Shibuya, M. Tyrosine Kinase Receptor Flt/VEGFR Family: Its Characterization Related to Angiogenesis and Cancer. *Genes Cancer* 1, 1119-1123 (2010).

58 Winder, T. & Lenz, H. J. Vascular endothelial growth factor and epidermal growth factor signaling pathways as therapeutic targets for colorectal cancer. *Gastroenterology* 138, 2163-2176 (2010).

59 Andrae, J., Gallini, R. & Betsholtz, C. Role of platelet-derived growth factors in physiology and medicine. *Genes Dev* 22, 1276-1312 (2008).

60 Abramsson, A., Lindblom, P. & Betsholtz, C. Endothelial and nonendothelial sources of PDGF-B regulate pericyte recruitment and influence vascular pattern formation in tumors. *J Clin Invest* 112, 1142-1151 (2003).

61 Betsholtz, C., Karlsson, L. & Lindahl, P. Developmental roles of platelet-derived growth factors. *Bioessays* 23, 494-507 (2001).

62 Board, R. & Jayson, G. C. Platelet-derived growth factor receptor (PDGFR): a target for anticancer therapeutics. *Drug Resist Updat* 8, 75-83 (2005).

63 Jones, A. V. & Cross, N. C. Oncogenic derivatives of platelet-derived growth factor receptors. *Cell Mol Life Sci* 61, 2912-2923 (2004).

64 Laird, A. D. et al. SU6668 is a potent antiangiogenic and antitumor agent that induces regression of established tumors. *Cancer Res* 60, 4152-4160 (2000).

65 Yamamoto, M. et al. TSU68 prevents liver metastasis of colon cancer xenografts by modulating the premetastatic niche. *Cancer Res* 68, 9754-9762 (2008).

66 Trzcinska-Daneluti, A. M. et al. High-content functional screen to identify proteins that correct F508del-CFTR function. *Mol Cell Proteomics* 8, 780-790 (2009).

67 Zabner, J., Zeiher, B. G., Friedman, E. & Welsh, M. J. Adenovirus-mediated gene transfer to ciliated airway epithelia requires prolonged incubation time. *J Virol* 70, 6994-7003 (1996).

68 Kim Chiaw, P. et al. Functional rescue of DeltaF508-CFTR by peptides designed to mimic sorting motifs. *Chem Biol* 16, 520-530 (2009).

69 Ostedgaard, L. S. et al. CFTR with a partially deleted R domain corrects the cystic fibrosis chloride transport defect in human airway epithelia in vitro and in mouse nasal mucosa in vivo. *Proc Natl Acad Sci USA* 99, 3093-3098 (2002).

We claim:

1. A method of treating cystic fibrosis (CF; mucoviscidosis) in a subject in need thereof, said method comprising administering to said subject, an effective amount of a compound of the formula III below including all stereoisomers, and polymorphs thereof, and combinations thereof:

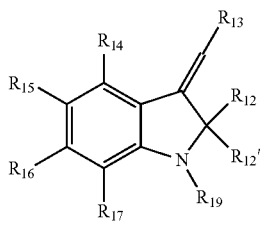

(III)

wherein
one of $R_{12}$ or $R_{12}'$ is —OR''' or —SR''' and the other of $R_{12}$ or $R_{12}'$ is H, and each R''' independently represents H, alkyl, cycloalkyl, aryl, heteroaryl or alkanoyl, or $R_{12}$ and $R_{12}'$ taken together is =O or =S;

$R_{13}$ is a five membered nitrogen containing heterocyclic aromatic ring, optionally substituted with one or more substituents independently selected from the group consisting of alkyl, cycloalkyl, alkoxy, cycloalkoxy, aryl, heteroaryl, aryloxy, heteroaryloxy, alkaryl, alkheteroaryl, alkaryloxy, alkheteroaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R and CONRR'; and n is 0-3; R is H, alkyl or aryl; and R' is H, alkyl or aryl;

$R_{14}$, $R_{15}$, $R_{16}$, and $R_{17}$ are each independently selected from the group consisting of H, alkyl, cycloalkyl, alkoxy, cycloalkoxy, aryl, heteroaryl, aryloxy, heteroaryloxy, alkaryl, alkheteroaryl, alkaryloxy, alkheteroaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R, and CONRR'; and n is 0-3; R is H, alkyl or aryl; and R' is H, alkyl or aryl; and $R_{19}$ is H, alkyl or cycloalkyl.

2. The method of claim 1, wherein
one of $R_{12}$ or $R_{12}'$ is —OR''' or —SR''' and the other of $R_{12}$ or $R_{12}'$ is H, and each R''' independently represents H, (C$_{1-20}$)-alkyl, (C$_{3-10}$)-cycloalkyl, (C$_{6-14}$)-aryl, (C$_{5-14}$)-heteroaryl or (C$_{1-20}$)-alkanoyl, or $R_{12}$ and $R_{12}'$ taken together is =O or =S;

$R_{13}$ is a five membered nitrogen containing heterocyclic aromatic ring, optionally substituted with one or more substituents independently selected from the group consisting of (C$_{1-20}$)-alkyl, (C$_{3-10}$)-cycloalkyl, (C$_{1-20}$)-alkoxy, (C$_{3-10}$)-cycloalkoxy, (C$_{6-14}$)-aryl, (C$_{5-14}$)-heteroaryl, (C$_{6-14}$)-aryloxy, (C$_{5-14}$)-heteroaryloxy, (C$_{1-20}$)-alk-(C$_{6-14}$)-aryl, (C$_{1-20}$)-alk-(C$_{5-14}$)-heteroaryl, (C$_{1-20}$)-alk-(C$_{6-14}$)-aryloxy, (C$_{1-20}$)-alk-(C$_{5-14}$)-heteroaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R and CONRR'; and n is 0-3; R is H, (C$_{1-20}$)-alkyl, (C$_{6-14}$)-aryl or (C$_{5-14}$)-heteroaryl; R' is H, (C$_{1-20}$)-alkyl, (C$_{3-10}$)-cycloalkyl, (C$_{6-14}$)-aryl or (C$_{5-14}$)-heteroaryl;

$R_{14}$, $R_{15}$, $R_{16}$, and $R_{17}$ are each independently selected from the group consisting of H, (C$_{1-20}$)-alkyl, (C$_{3-10}$)-cycloalkyl, (C$_{1-20}$)-alkoxy, (C$_{3-10}$)-cycloalkoxy, (C$_{6-14}$)-aryl, (C$_{5-14}$)-heteroaryl, (C$_{6-14}$)-aryloxy, (C$_{5-14}$)-heteroaryloxy, (C$_{1-20}$)-alk-(C$_{6-14}$)-aryl, (C$_{1-20}$)-alk-(C$_{5-14}$)-heteroaryl, (C$_{1-20}$)-alk-(C$_{6-14}$)-aryloxy, (C$_{1-20}$)-alk-(C$_{5-14}$)-heteroaryloxy, halogen, trihalomethyl, S(O)R, SO$_2$NRR', SO$_3$R, SR, NO$_2$, NRR', OH, CN, C(O)R, OC(O)R, NHC(O)R, (CH$_2$)$_n$CO$_2$R and CONRR'; and n is 0-3; R is H, (C$_{1-20}$)-alkyl, (C$_{6-14}$)-aryl or (C$_{5-14}$)-heteroaryl; R' is H, (C$_{1-20}$)-alkyl, (C$_{3-10}$)-cycloalkyl, (C$_{6-14}$)-aryl or (C$_{5-14}$)-heteroaryl; and $R_{19}$ is H, (C$_{1-20}$)-alkyl or (C$_{3-10}$)-cycloalkyl.

3. The method according to claim 1 wherein the compound of formula III is 3-[4-methyl-2-[(Z)-(2-oxo-1H-indol-3-ylidene)methyl]-1H-pyrrol-3-yl]propanoic acid (i.e. SU5402) of the formula IV below including all stereoisomers, and polymorphs thereof, and combinations thereof:

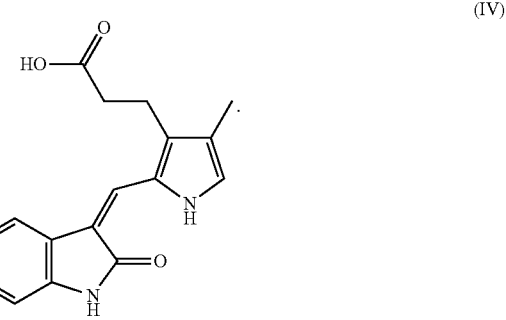

(IV)

4. The method according to claim 1 wherein the compound of formula III is 3-[2,4-dimethyl-5-[(Z)-(2-oxo-1H-indol-3-ylidene)methyl]-1H-pyrrol-3-yl]propanoic acid (i.e. SU6668) of the formula V below including all stereoisomers, and polymorphs, and combinations thereof:

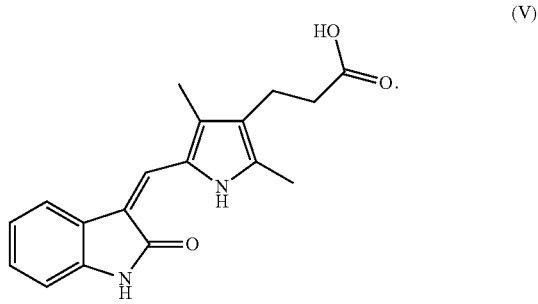 [SMILES: Cc1[nH]c(/C=C2\C(=O)Nc3ccccc32)c(C)c1CCC(=O)O]

(V)

5. The method according to claim 1, wherein the compound of formulae III, IV or V is administered in a medicament in the form of gelatine capsules, tablets, SC tablets or capsules.

6. The method according to claim 1, wherein the compound of formulae III, IV or V is administered in a medicament prepared for parenteral or intravenous administration, in the form of a solution.

7. The method according to claim 1, wherein the compound of formulae III, IV or V is administered in a medicament prepared for administration in the form of an aerosol.

* * * * *